(12) United States Patent
Cong et al.

(10) Patent No.: US 9,882,420 B2
(45) Date of Patent: *Jan. 30, 2018

(54) SENSING TEMPERATURE WITHIN MEDICAL DEVICES

(71) Applicant: Medtronic, Inc., Minneapolis, MN (US)

(72) Inventors: Peng Cong, Burlingame, CA (US); Venkat R. Gaddam, Maple Grove, MN (US); David P. Olson, Minnetrista, MN (US); Erik R. Scott, Maple Grove, MN (US); Todd V. Smith, Shoreview, MN (US); Leroy L. Perz, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/464,066

(22) Filed: Mar. 20, 2017

(65) Prior Publication Data

US 2017/0194810 A1 Jul. 6, 2017

Related U.S. Application Data

(63) Continuation of application No. 13/783,761, filed on Mar. 4, 2013, now Pat. No. 9,653,935.

(51) Int. Cl.
*H02J 7/00* (2006.01)
*H02J 7/04* (2006.01)
(Continued)

(52) U.S. Cl.
CPC ............ *H02J 7/047* (2013.01); *H02J 7/007* (2013.01); *H02J 7/0091* (2013.01); *H02J 7/025* (2013.01);
(Continued)

(58) Field of Classification Search
CPC .......... H02J 7/007; H02J 7/025; H02J 7/0091; A61N 1/3787; G01K 11/006; G01K 11/20
(Continued)

(56) References Cited

U.S. PATENT DOCUMENTS

| 4,819,658 A | 4/1989 | Kolodner |
| 5,350,413 A | 9/1994 | Miller |

(Continued)

FOREIGN PATENT DOCUMENTS

| CN | 87207763 U | 1/1988 |
| CN | 1263621 A | 8/2000 |

(Continued)

OTHER PUBLICATIONS

First Office Action, and translation thereof, from counterpart Chinese Application No. 201380032161.2, dated Dec. 18, 2014, 26 pp.

(Continued)

*Primary Examiner* — Nathaniel Pelton
(74) *Attorney, Agent, or Firm* — Shumaker & Sieffert, P.A.

(57) ABSTRACT

Devices, systems, and techniques for monitoring the temperature of a device used to charge a rechargeable power source are disclosed. Implantable medical devices may include a rechargeable power source that can be transcutaneously charged. The temperature of an external charging device and/or an implantable medical device may be monitored to control the temperature exposure to patient tissue. In one example, a temperature sensor may sense a temperature of a portion of a device, wherein the portion is non-thermally coupled to the temperature sensor. A processor may then control charging of the rechargeable power source based on the sensed temperature.

22 Claims, 13 Drawing Sheets

Related U.S. Application Data

(60) Provisional application No. 61/636,304, filed on Apr. 20, 2012.

(51) Int. Cl.

| | | |
|---|---|---|
| *H02J 7/02* | (2016.01) | |
| *A61N 1/378* | (2006.01) | |
| *G01K 11/20* | (2006.01) | |
| *G01K 11/00* | (2006.01) | |

(52) U.S. Cl.
CPC .......... *A61N 1/3787* (2013.01); *G01K 11/006* (2013.01); *G01K 11/20* (2013.01)

(58) Field of Classification Search
USPC ................................................ 320/150–154
See application file for complete search history.

(56) References Cited

U.S. PATENT DOCUMENTS

| | | | |
|---|---|---|---|
| 5,733,313 A * | 3/1998 | Barreras, Sr. ............ A61N 1/08 128/903 |
| 6,386,757 B1 | 5/2002 | Konno | |
| 6,772,011 B2 | 8/2004 | Dolgin | |
| 7,225,032 B2 | 5/2007 | Schmeling et al. | |
| 7,336,055 B2 | 2/2008 | Ishishita | |
| 8,006,626 B2 * | 8/2011 | Kumar ................ H01M 10/625 105/49 |
| 8,036,731 B2 | 10/2011 | Kimchy et al. | |
| 8,169,189 B2 | 5/2012 | Eto | |
| 8,695,430 B1 * | 4/2014 | Eldridge ................ G01K 11/20 73/700 |
| 8,961,004 B2 * | 2/2015 | Srinivasan .............. H01M 2/34 320/150 |
| 9,151,811 B2 | 10/2015 | Jester et al. | |
| 9,337,684 B2 | 5/2016 | Rizzo | |
| 2004/0013325 A1 | 1/2004 | Cook | |
| 2004/0133251 A1 * | 7/2004 | Altshuler ............ A61B 18/203 607/88 |
| 2005/0275383 A1 * | 12/2005 | Ishishita ................ G01K 15/00 320/150 |
| 2008/0136372 A1 | 6/2008 | Eto | |
| 2008/0272742 A1 * | 11/2008 | Hart .................... H01M 10/443 320/150 |
| 2009/0112291 A1 * | 4/2009 | Wahlstrand .......... A61N 1/3787 607/61 |
| 2010/0256708 A1 | 10/2010 | Thornton et al. | |
| 2011/0022125 A1 | 1/2011 | Olson et al. | |
| 2011/0057624 A1 * | 3/2011 | Rizzo .................... H02J 7/0075 320/152 |
| 2011/0288607 A1 * | 11/2011 | Cholette .................. A61B 5/01 607/18 |
| 2011/0299565 A1 * | 12/2011 | Jester .................... G01R 33/285 374/161 |
| 2012/0235634 A1 * | 9/2012 | Hall ........................ H03H 7/40 320/108 |
| 2013/0278226 A1 | 10/2013 | Cong et al. | |

FOREIGN PATENT DOCUMENTS

| | | |
|---|---|---|
| CN | 100346528 C | 10/2007 |
| CN | 101142734 A | 3/2008 |
| CN | 102077439 A | 5/2011 |
| CN | 102341038 A | 2/2012 |

OTHER PUBLICATIONS

International Search Report and Written Opinion, Intl Application No. PCT/US2013/029783, dated Feb. 25, 2014, 8 pages.

Notice on the Second Office Action, and translation thereof, from counterpart Chinese Application No. 201380032161.2, dated Jan. 19, 2017, 32 pp.

Examination Report from counterpart European Application No. 13712416.0, dated Dec. 13, 2016, 5 pp.

International Preliminary Report on Patentability from International Application No. PCT/US2013/029873 dated Oct. 21, 2014, 6 pp.

Prosecution History from U.S. Appl. No. 13/783,761 dated Mar. 4, 2013 through Apr. 26, 2017, 154 pp.

Amendments received before Examination from counterpart European Application No. 13712416.0 filed Nov. 14, 2014, 10 pp.

Response to Examination Report from counterpart European Application No. 13712416.0 dated Dec. 13, 2016, filed Jun. 22, 2017, 7 pp.

Notice on the Third Office Action, and translation thereof, from counterpart Chinese Application No. 201380032161.2, dated Sep. 13, 2017, 21 pp.

* cited by examiner

SENSING TEMPERATURE WITHIN MEDICAL DEVICES

This application is a continuation application of U.S. patent application Ser. No. 13/783,761, filed Mar. 4, 2013, which claims priority to provisionally-filed U.S. Patent Application Ser. No. 61/636,304, filed Apr. 20, 2012, both of which are incorporated herein by reference in their entirety.

TECHNICAL FIELD

The disclosure relates to medical devices and, more particularly, temperature sensors for sensing temperature of medical devices.

BACKGROUND

Implantable medical devices (IMDs) may be used to monitor a patient condition and/or deliver therapy to the patient. In long term or chronic uses, IMDs may include a rechargeable power source (e.g., comprising one or more capacitors or batteries) that extends the operational life of the medical device to weeks, months, or even years over a non-rechargeable device.

When the energy stored in the rechargeable power source has been depleted, the patient may use an external charging device to recharge the power source. Since the rechargeable power source is implanted in the patient and the charging device is external to the patient, this charging process may be referred to as transcutaneous charging. In some examples, transcutaneous charging may be performed via inductive coupling between a primary coil in the charging device and a secondary coil in the IMD.

When a current is applied to the primary coil and the primary coil is aligned with the secondary coil, electrical current is induced in the secondary coil within the patient. Circuitry associated with the IMD uses the current to charge a rechargeable power source, such as a battery, within the IMD. Therefore, the external charging device does not need to physically connect with the rechargeable power source for charging to occur.

SUMMARY

In general, the disclosure is directed to devices, systems, and techniques for monitoring the temperature of a medical device used to charge a rechargeable power source. An implantable medical device (IMD) may include a rechargeable power source that can be transcutaneously charged. The IMD, an external charging device, or other medical device associated with charging the rechargeable power source may include a temperature sensor for monitoring the temperature of the medical device during a charging session. The temperature may be monitored to control charging of the rechargeable power source and/or avoid exposing patient tissue to undesirable temperatures.

The temperature sensor may be configured to sense the temperature of a portion of the device being monitored without being thermally-coupled to this portion of the device being monitored for temperature changes. In other words, the temperature sensor may utilize indirect temperature measurement techniques to sense the temperature of a particular surface or material within a device.

In one aspect, the disclosure is directed to a method that includes sensing, by a temperature sensor, a temperature of a portion of a medical device, wherein the portion is non-thermally coupled to the temperature sensor, and controlling charging of a rechargeable power source based on the sensed temperature.

Another method may comprise sensing a temperature of a portion of a medical device by a temperature sensor and controlling charging of a rechargeable power source based on the sensed temperature, wherein the temperature sensor is configured to sense the temperature of the portion without being thermally-coupled to the portion.

In another aspect, the disclosure is directed to a system that includes a medical device that includes a housing, a temperature sensor disposed within the housing and configured to sense a temperature of a portion of the medical device, wherein the portion is non-thermally coupled to the temperature sensor, and a processor configured to control charging of a rechargeable power source based on the sensed temperature.

The disclosure may be directed a system. The system may include a medical device comprising a housing. A temperature sensor may be disposed within the housing and configured to sense a temperature of a portion of the medical device, wherein the temperature sensor is configured to be non-thermally coupled to the portion. At least one processor may be configured to control charging of a rechargeable power source based on the sensed temperature.

In another aspect, the disclosure is directed to a system that includes means for sensing a temperature of a portion of a medical device, wherein the portion is non-thermally coupled to the means for sensing the temperature and means for controlling charging of a rechargeable power source based on the sensed temperature.

In a further aspect, the disclosure is directed to a non-transitory computer-readable storage medium including instructions that cause at least one processor to sense a temperature of a portion of a device, wherein the portion is non-thermally coupled to the temperature sensor, and control charging of a rechargeable power source based on the sensed temperature.

The details of one or more example are set forth in the accompanying drawings and the description below. Other features, objects, and advantages will be apparent from the description and drawings, and from the claims.

DETAILED DESCRIPTION

Figure 1:
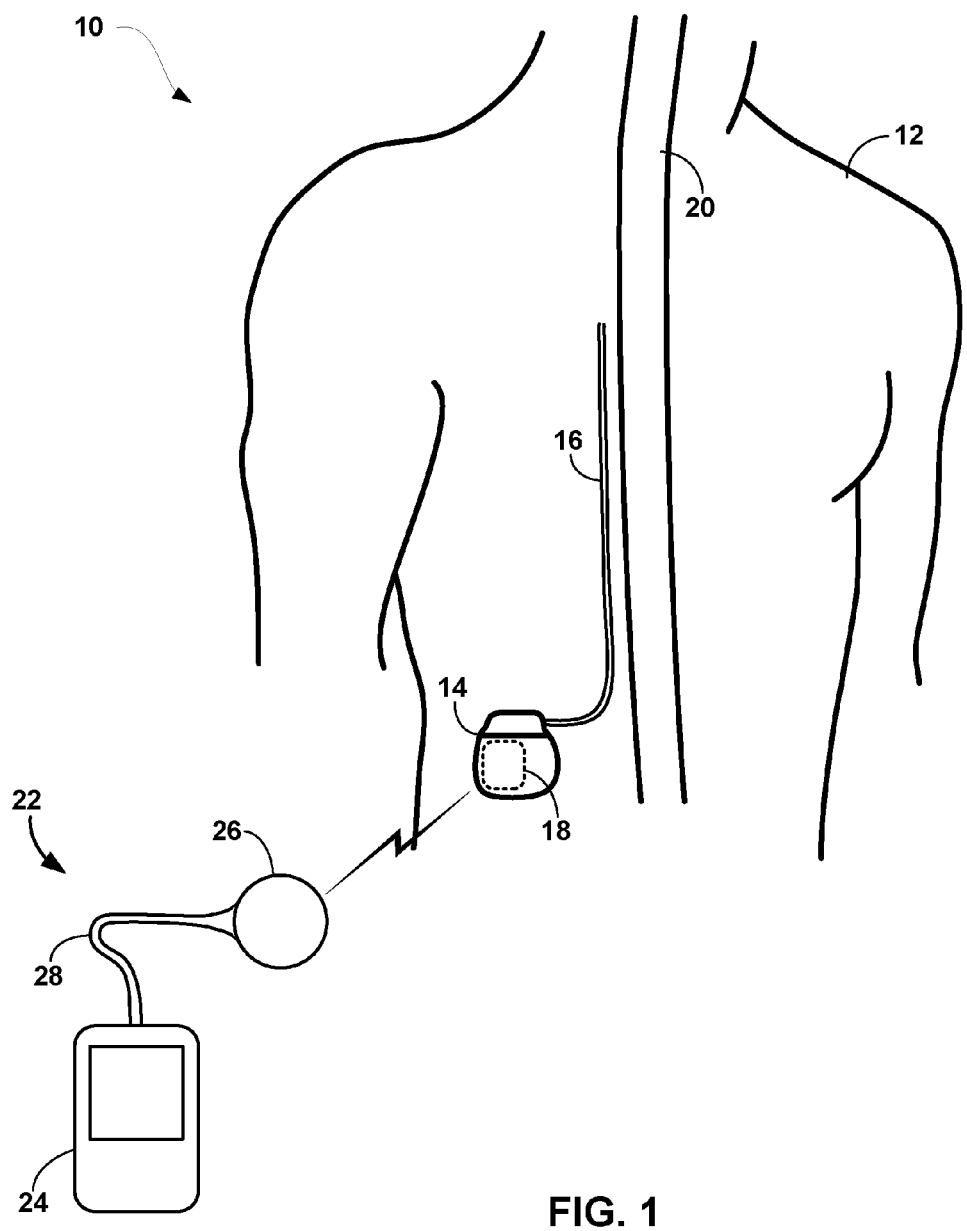
FIG. 1 is a conceptual diagram illustrating an example system that includes an implantable medical device (IMD) and an external charging device that charges a rechargeable power source of the IMD.

This disclosure is generally directed to devices, systems, and techniques for monitoring the temperature occurring during recharge of a rechargeable power source. Implantable medical devices (IMDs) may be implanted within a patient and used to monitor a parameter of the patient and/or deliver a therapy to the patient. To extend the operational life of the IMD, the IMD may include a rechargeable power source (e.g., one or more capacitors or batteries). When the rechargeable power source is being recharged, the power transmitted to the IMD may generate heat that increases the temperature of the IMD. In addition, an external charging device (e.g., another medical device) placed against the skin of the patient may increase in temperature when power is transmitted during the recharging session. This may result in heating of tissue proximate the IMD and/or proximate the external charging device. In order to prevent undesirable temperatures, the system may monitor sensed temperatures in the IMD and/or external charging device.

An IMD may include a temperature sensor, such as a thermocouple or thermistor, physically attached and thermally coupled to the surface of a target component (e.g., the component of which temperature is to be sensed) within the IMD. Alternatively, a thermocouple, thermistor, or other temperature sensor, may be disposed within an IMD to sense the ambient temperature within the IMD. However, thermocouples directly coupled to a desired surface (e.g., an interior surface of the IMD housing) may be difficult and/or expensive to manufacture, and ambient temperature sensors may not accurately measure different temperatures at specific regions of the IMD or portions that transfer heat to the patient.

As disclosed herein, a medical device associated with charging an implantable rechargeable power source (e.g., an IMD or an external charging device) may include one or more non-thermally coupled temperature sensors. In particular, the temperature sensor is not thermally coupled, and need not be directly attached, to the portion of the device from which temperature is to be measured. In cases in which the temperature sensor is not attached to the portion of the device from which the temperature is to be measured, it may be said the temperature sensor is remotely located from that portion. The non-thermally coupled temperature sensor may utilize indirect temperature measurement techniques to sense and measure the temperature of locations within the device that are non-thermally coupled with the temperature sensor. For example, the temperature sensor may be an infrared (IR) temperature sensor mounted on a printed circuit board (PCB), hybrid board, or other location within the device. The temperature sensor may then be oriented to sense a temperature of a surface of a structure, component, or housing of the medical device (e.g., the housing of the IMD or the external charging device) to sense the temperature at that surface. In other examples, as alternatives to infrared sensing, the temperature sensor may utilize phosphor thermometry or pressure measurements to sense the temperature of non-thermally coupled portions of the device.

A non-thermally coupled temperature sensor may be directed, positioned, or otherwise oriented toward a specific portion of a medical device or component of the medical device to sense the temperature at that particular surface. Since devices may have varying temperatures throughout the device due to different components, materials, and/or dimensions of the device, in some examples, the device may use multiple temperature sensors to identify these different temperatures instead of sensing a single general temperature of the device. In other examples, the medical device may include a heat pipe, light pipe, or other energy transfer element that conducts energy from a desired surface of the device to the location of the temperature sensor. In some examples, the device may include a phase change material configured to reduce temperature variations and provide a single surface for a temperature sensor to sense the temperature. The phase change material may, in some examples, be in physical contact with the portion of the device from which temperature is desired to be sensed.

In addition to providing temperature measurements of specific locations within a device, non-thermally coupled temperature sensors may also reduce manufacturing complexity. For example, one or more temperature sensors may be mounted to a printed circuit board or hybrid board and oriented towards the desired surface (e.g., a surface of the housing) for temperature measurement. When the housing is installed around the board and the temperature sensors, no components need to be mounted to the housing to achieve the desired temperature measurement. Therefore, non-thermally coupled temperature sensors may reduce assembly time, complexity, and cost.

In this manner, one or more non-thermally coupled temperature sensors may be used to provide temperature feedback for controlling the charging of the implanted rechargeable power source. The IMD and/or external charging device may monitor one or more temperatures to control charging and effectively limit temperatures of patient tissue adjacent the IMD and/or external charging device. For example, one or more processors may reduce the power used during the charging session, cycle the power to control heat imparted to tissue (e.g., cycle it on and off), or terminate the charging session. In another example, the processor may command a user interface to present a notification to the user to exchange the phase change material cartridge of the external charging device when the temperature indicates the temperature controlling properties of the cartridge have been exhausted. In other examples, the temperature sensed by a non-thermally coupled temperature sensor may be used to perform other or additional functions. For example, a processor may compare the sensed temperature to a fault condition threshold and disconnect the rechargeable power source from at least one electrical circuit when the sensed temperature exceeds the fault condition threshold.

FIG. 1 is a conceptual diagram illustrating an example system 10 that includes implantable medical device (IMD) 14 and external charging device 22 that charges rechargeable power source 18 of IMD 14. Although the techniques described in this disclosure are generally applicable to a variety of medical devices including medical devices such as patient monitors, electrical stimulators, or drug delivery devices, application of such techniques to implantable neurostimualtors will be described for purposes of illustration. More particularly, the disclosure will refer to an implantable neurostimulation system for use in spinal cord stimulation therapy, but without limitation as to other types of medical devices.

As shown in FIG. 1, system 10 includes an IMD 14 and external charging device 22 shown in conjunction with a patient 12, who is ordinarily a human patient. In the example of FIG. 1, IMD 14 is an implantable electrical stimulator that delivers neurostimulation therapy to patient 12, e.g., for relief of chronic pain or other symptoms. Generally IMD 14 may be a chronic electrical stimulator that remains implanted within patient 12 for weeks, months, or even years. In the example of FIG. 1, IMD 14 and lead 16 may be directed to delivering spinal cord stimulation therapy. In other examples, IMD 14 may be a temporary, or trial, stimulator used to screen or evaluate the efficacy of electrical stimulation for chronic therapy. IMD 14 may be implanted in a subcutaneous tissue pocket, within one or more layers of muscle, or other internal location. IMD 14 includes rechargeable power source 18, such as a rechargeable battery, and IMD 14 is coupled to lead 16.

Electrical stimulation energy, which may be constant current or constant voltage based pulses, for example, is delivered from IMD 14 to one or more targeted locations within patient 12 via one or more electrodes (not shown) of lead 16. The parameters for a program that controls delivery of stimulation energy by IMD 14 may include information identifying which electrodes have been selected for delivery of stimulation according to a stimulation program, the polarities of the selected electrodes, i.e., the electrode configuration for the program, and voltage or current amplitude, pulse rate, pulse shape, and pulse width of stimulation delivered by the electrodes. Electrical stimulation may be delivered in the form of stimulation pulses or continuous waveforms, for example.

In the example of FIG. 1, lead 16 is disposed within patient 12, e.g., implanted within patient 12. Lead 16 tunnels through tissue of patient 12 from along spinal cord 20 to a subcutaneous tissue pocket or other internal location where IMD 14 is disposed. Although lead 16 may be a single lead, lead 16 may include a lead extension or other segments that may aid in implantation or positioning of lead 16. In addition, a proximal end of lead 16 may include a connector (not shown) that electrically couples to a header of IMD 14. Although only one lead 16 is shown in FIG. 1, system 10 may include two or more leads, each coupled to IMD 14 and directed to similar or different target tissue sites. For example, multiple leads may be disposed along spinal cord 20 or leads may be directed to spinal cord 20 and/or other locations within patient 12.

Lead 16 may carry one or more electrodes that are placed adjacent to the target tissue, e.g., spinal cord 20 for spinal cord stimulation (SCS) therapy. One or more electrodes may be disposed at a distal tip of lead 16 and/or at other positions at intermediate points along lead 16, for example. Electrodes of lead 16 transfer electrical stimulation generated by an electrical stimulation generator in IMD 14 to tissue of patient 12. The electrodes may be electrode pads on a paddle lead, circular (e.g., ring) electrodes surrounding the body of the lead, conformable electrodes, cuff electrodes, segmented electrodes, or any other type of electrodes capable of forming unipolar, bipolar or multipolar electrode configurations for therapy. In general, ring electrodes arranged at different axial positions at the distal ends of lead 16 will be described for purposes of illustration.

In alternative examples, lead 16 may be configured to deliver stimulation energy generated by IMD 14 to stimulate one or more sacral nerves of patient 12, e.g., sacral nerve stimulation (SNS). SNS may be used to treat patients suffering from any number of pelvic floor disorders such as pain, urinary incontinence, fecal incontinence, sexual dysfunction, or other disorders treatable by targeting one or more sacral nerves. Lead 16 and IMD 14 may also be configured to provide other types of electrical stimulation or drug therapy (e.g., with lead 16 configured as a catheter). For example, lead 16 may be configured to provide deep brain stimulation (DBS), peripheral nerve stimulation (PNS), gastric stimulation to treat obesity or gastroparesis, tibial nerve stimulation, or other deep tissue or more superficial types of electrical stimulation. In other examples, lead 16 may provide one or more sensors configured to allow IMD 14 to monitor one or more parameters of patient 12. The one or more sensors may be provided in addition to, or in place of, therapy delivery by lead 16.

IMD 14 delivers electrical stimulation therapy to patient 12 via selected combinations of electrodes carried by lead 16. The target tissue for the electrical stimulation therapy may be any tissue affected by electrical stimulation energy, which may be in the form of electrical stimulation pulses or waveforms. In some examples, the target tissue includes nerves, smooth muscle, and skeletal muscle. In the example illustrated by FIG. 1, the target tissue for electrical stimulation delivered via lead 16 is tissue proximate spinal cord 20 (e.g., one or more target locations of the dorsal columns or one or more dorsal roots that branch from spinal cord 20. Lead 16 may be introduced into spinal cord 20 via any suitable region, such as the thoracic, cervical or lumbar regions. Stimulation of dorsal columns, dorsal roots, and/or peripheral nerves may, for example, prevent pain signals from traveling through spinal cord 20 and to the brain of the patient. Patient 12 may perceive the interruption of pain signals as a reduction in pain and, therefore, efficacious therapy results. For treatment of other disorders, lead 16 may be introduced at any exterior location of patient 12.

Although lead 16 is described as generally delivering or transmitting electrical stimulation signals, lead 16 may additionally or alternatively transmit electrical signals from patient 12 to IMD 14 for monitoring. For example, IMD 14 may utilize detected nerve impulses to diagnose the condition of patient 12 or adjust the delivered stimulation therapy. Lead 16 may thus transmit electrical signals to and from patient 12.

A user, such as a clinician or patient 12, may interact with a user interface of an external programmer (not shown) to program IMD 14. Programming of IMD 14 may refer generally to the generation and transfer of commands, programs, or other information to control the operation of IMD 14. For example, the external programmer may transmit programs, parameter adjustments, program selections, group selections, or other information to control the operation of IMD 14, e.g., by wireless telemetry or wired connection.

In some cases, an external programmer may be characterized as a physician or clinician programmer if it is primarily intended for use by a physician or clinician. In other cases, the external programmer may be characterized as a patient programmer if it is primarily intended for use by a patient. A patient programmer is generally accessible to patient 12 and, in many cases, may be a portable device that may accompany the patient throughout the patient's daily routine. In general, a physician or clinician programmer may support selection and generation of programs by a clinician for use by stimulator 14, whereas a patient programmer may support adjustment and selection of such programs by a patient during ordinary use. In other examples, external charging device 22 may be included with, or form part of, an external programmer. In this manner, a user such as a clinician, other caregiver, or patient may program and charge IMD 14 using one device, or multiple devices.

IMD 14 may be constructed of any polymer, metal, or composite material sufficient to house the components of IMD 14 (e.g., components illustrated in FIG. 2) within patient 12. In this example, IMD 14 may be constructed with a biocompatible housing, such as titanium or stainless steel, or a polymeric material such as silicone or polyurethane, and surgically implanted at a site in patient 12 near the pelvis, abdomen, or buttocks. The housing of IMD 14 may be configured to provide a hermetic seal for components, such as rechargeable power source 18. In addition, the housing of IMD 14 may be selected of a material that facilitates receiving energy to charge rechargeable power source 18.

As described herein, rechargeable power source 18 may be included within IMD 14. However, in other examples, rechargeable power source 18 could be located external to a housing of IMD 14, separately protected from fluids of patient 12, and electrically coupled to electrical components of IMD 14. This type of configuration of IMD 14 and rechargeable power source 18 may provide implant location flexibility when anatomical space for implantable devices is minimal. In any case, rechargeable power source 18 may provide operational electrical power to one or more components of IMD 14.

Rechargeable power source 18 may include one or more capacitors, batteries, or components (e.g. chemical or electrical energy storage devices). Example batteries may include lithium-based batteries, nickel metal-hydride batteries, or other materials. Rechargeable power source 18 is also rechargeable. In other words, rechargeable power source 18 may be replenished, refilled, or otherwise capable of increasing the amount of energy stored after energy has been depleted. Rechargeable power source 18 may be subjected to numerous discharge and recharge cycles (e.g., hundreds or even thousands of cycles) over the life of rechargeable power source 18 in IMD 14. Rechargeable power source 18 may be recharged when fully depleted or partially depleted.

Charging device 22 may be used to recharge rechargeable power source 18 and IMD 14 when implanted in patient 12. Charging device 22 may be a hand-held device, a portable device, or a stationary charging system. In any case, charging device 22 may include components necessary to charge rechargeable power source 18 through tissue of patient 12. For example, charging device 22 may include housing 24, charging cable 28, and charging head 26. Housing 24 may enclose or house at least some of the operational components of charging device 22. For example, housing 24 may include a user interface, processor, memory, power source, and other components. Charging cable 28 may electrically couple charging head 26 to the power source within housing 24, such that charging cable 28 is configured to transmit power and/or information to charging head 26. Charging head 26 may include a coil (e.g., a component of charging head 26) for inductive coupling or components used to transmit power from charging head 26 to rechargeable power source 18. In other examples, charging cable 28 and/or charging head 26 may also be contained within or disposed on housing 24, or various ones of the components associated with charging device 22 may be carried by cable 28 and/or charging head 26. Although a user may control the recharging process with a user interface of charging device 22, charging device may alternatively be controlled by another device (e.g., an external programmer).

In some examples, charging device 22 may only perform charging of rechargeable power source 18. In other examples, charging device 22 may be an external programmer or other device configured to perform additional functions. For example, when embodied as an external programmer, charging device 22 may transmit programming commands to IMD 14 in addition to charge rechargeable power source 18. In another example, charging device 22 may communicate with IMD 14 to transmit and/or receive information related to the charging of rechargeable power source 18. For example, IMD 14 may transmit information regarding temperature of IMD 14 and/or rechargeable power source 18, received power during charging, the charge level of rechargeable power source 18, charge depletion rates during use, or any other information related to power consumption and recharging of IMD 14 and rechargeable power source 18.

Charging device 22 and IMD 14 may utilize any wireless power transfer techniques that are capable of recharging rechargeable power source 18 of IMD 14 when IMD 14 is implanted within patient 14. In one example, system 10 may utilize inductive coupling between a coil of charging device 22 (e.g., a coil within charging head 26) and a coil of IMD 14 coupled to rechargeable power source 18. In inductive coupling, charging device 22 is placed near implanted IMD 14 such that a primary coil of charging device 22 is aligned with, i.e., placed over, a secondary coil of IMD 14. Charging device 22 may then generate an electrical current in the primary coil based on a selected power level for charging rechargeable power source 18. As described further below, the power level may be selected to control the temperature of IMD 14 and/or the charge rate of rechargeable power source 18. When the primary and secondary coils are aligned, the electrical current in the primary coil may magnetically induce an electrical current in the secondary coil within IMD 14. Since the secondary coil is associated with and electrically coupled to rechargeable power source 18, the induced electrical current may be used to increase the voltage, or charge level, of rechargeable power source 18. Although inductive coupling is generally described herein, any type of wireless energy transfer may be used to charge rechargeable power source 18.

During the energy transfer process that charges rechargeable power source 18, some of the energy involved in the charging process may be converted into heat at rechargeable power source 18, other components of IMD 14, and/or in charging head 26, for example. When increased energy levels are used to charge rechargeable power source 18 at a higher rate, the temperature of IMD 14 and/or charging device 22 may also increase. Although the temperature of the IMD 14 housing may not achieve a temperature sufficient to burn or necrose tissue adjacent to the housing of IMD 14, elevated temperatures may be undesirable and could cause discomfort in some cases. Therefore, one or more devices may monitor temperatures of any device or component that may come into contact with or otherwise affect tissue of patient 12. The sensed temperature may be used as feedback in a closed-loop or partially closed-loop temperature control system. For example, charging device 22 may control the power level, power cycle times, and/or charging time used to charge rechargeable power source 18 to reduce or minimize any undesirable temperatures of IMD 14 that could be caused by charging rechargeable power source 18. In addition, monitoring the temperature of IMD 14 and/or the temperature of tissue adjacent to the housing of IMD 14 may minimize patient discomfort during the charging process.

As described herein, system 10 may utilize one or more temperature sensors to sense, measure, or otherwise detect the temperature of a portion of a device non-thermally coupled to the temperature sensor. In one example, a temperature sensor of system 10 may sense the temperature of a portion of a medical device (e.g., charging head 26 or IMD 14). The portion of the medical device may be non-thermally coupled to the temperature sensor. A processor of system 10 (e.g., a processor housed by either charging device 22 or IMD 14) may be configured to control charging of rechargeable power source 18 based on the sensed temperature. In this manner, the non-thermally coupled temperature sensor may provide feedback for controlling the charging of rechargeable power source 18. For example, charging device 22 may control current applied to a primary coil within charging head 26 based on the sensed temperature. Charging device 22 may control current, for example, by controlling a current amplitude, duty cycle, or other characteristic of the charging current. In some examples, the temperature sensor may be disposed within a housing of the medical device (e.g., a housing of charging head 26, housing 24, or a housing of IMD 14). In this manner, the temperature sensor may be disposed in a medical device that is either external to patient 12 or implanted within patient 12.

The temperature sensors (e.g., non-thermally coupled or non-contact sensors) discussed herein are generally described as non-thermally coupled to the portion or surface of a structure to be sensed. In other words, the temperature sensor may not use physical contact or other direct measurements to sense temperature of the desired portion of the medical device. Although the temperature sensor may be physically connected or mounted, through one or more members, to the portion of the medical device from which the temperature is sensed, the temperature of the portion is not sensed or measured through this physical connection. For example, the temperature sensor may be mounted on a hybrid board of IMD 14, the hybrid board may be mounted to a surface of the IMD housing, and the temperature sensor may sense the temperature of a portion of the IMD housing. However, the temperature sensor may sense the temperature of the portion of the IMD housing through a medium other than the hybrid board (e.g., through a vacuum, air, or another gas separating the temperature sensor from the portion of the IMD housing).

Non-thermally coupled temperature sensors described herein may take different forms and utilize different temperature sensing techniques. In one example, a temperature sensor may be an infrared temperature sensor. The infrared temperature sensor may be configured to sense a level of infrared radiation emitted from the portion of the medical device. Generally, the intensity of the IR energy emitted from an object increases or decreases in proportion to its temperature. In addition, the IR energy emitted from the object may be affected by the emissivity of the material of the object. Therefore, an IR temperature sensor used within system 10 may be calibrated to the specific material of the object from which the IR energy will be detected. In any case, an IR temperature sensor may be described as a non-thermally coupled or non-contact temperature sensor.

In other examples, a non-thermally coupled temperature sensor may utilize phosphor thermometry. This type of temperature sensor may include an emitter component and a detector component. The emitter may be configured to emit electromagnetic radiation toward a desired surface. The temperature sensor then excites, with the emitted electromagnetic radiation, a phosphor material disposed on the portion of the object that will be measured. In other words, the object from which temperature will be sensed may be coated with the phosphor material. A detector of the temperature sensor, in this example, may be configured to detect a phase shift in a luminescence emitted from the phosphor material in response to the excitation. The temperature sensor may then be configured to determine the temperature of the portion of the object based on the detected phase shift. In some examples, the temperature sensor may output a signal representative of the detected phase shift, and a processor is configured to determine the temperature based on the signal output from the sensor.

Non-thermally coupled temperature sensors may also utilize other detectable changes to determine changes in temperature of a medical device. For example, a temperature sensor may measure changes to pressure within the device. In a hermetically sealed medical device, changes in temperature of the device may cause a proportional change in the internal pressure of the device. For example, an increase in pressure may indicate an increase in temperature of the device. Therefore, a temperature sensor may sense or measure changes to air pressure within the device to sense temperature changes of the device. Since pressure changes outside of the device may need to be used to calibrate the internal pressure changes, system 10 may utilize pressure measurements obtained by charging device 22, for example, to correct changes to pressure measured within a device.

The non-thermally coupled temperature sensors described herein may be mounted anywhere within the device. In one example, the temperature sensor may be mounted to a printed circuit board within a housing of the medical device (e.g. charging head 26, housing 24, or IMD 14). From the location on the printed circuit board, the temperature sensor may be oriented to sense the temperature of a desired portion of the device (e.g., using infrared sensing, phosphor thermometry, or pressure sensing, as described above). In some examples, this portion to be sensed may be a part of the housing, a recharge coil, or any other components within the medical device (e.g., IMD 14 or external charging device 22). In other examples, the temperature sensor may be mounted to a hybrid board or a separate mounting platform within the device. In alternative examples, the temperature sensor may be mounted to the housing of the device and oriented to sense the temperature of a component within the device or another non-thermally coupled portion of the housing.

System 10 may utilize one or more non-thermally coupled temperature sensors in one or more medical device. For example, each of charging head 26 and IMD 14 may include a single temperature sensor. In another example, each of charging head 26 (e.g., external of patient 12) and/or IMD 14 (e.g., implanted within patient 12) may include two or more temperature sensors. Multiple temperature sensors within the same device may be provided for different reasons. For example, each of the multiple temperature sensors may be oriented to sense the temperature of the same portion of the device for redundant, backup, composite, or cross-correlated temperature measurement. If multiple non-thermally coupled temperature sensors are used, the multiple sensors may be similar or may instead be sensors of different types of non-thermally coupled temperatures sensors described herein.

Alternatively, two temperature sensors may be oriented to sense temperature of different surfaces and/or components within the same device. A first temperature sensor may be configured to sense a first portion of the device and a second temperature sensor may be configured to sense a second portion of the device. The two portions may be of different components or different areas of the same component. In one example, the first portion may be a one housing surface within the device, and the second portion may be another housing surface within the device. Since temperatures within a device may be non-uniform due to component location, thermal transfer within the device, or other external factors, the multiple temperature sensors may be used to identify temperature variations or "hot spots" of the device. In some cases, a one or multi-dimension array of temperature sensors may be provided to sense one or more portions of the IMD 14 or external device (e.g., recharger).

In some examples, two surfaces being sensed for temperature may be located adjacent to one another (e.g., different locations of a generally planar surface). In this example, two temperature sensors may be mounted to the same side of a hybrid board and oriented toward their respective surfaces. In other examples, the two surfaces may be generally opposed to one another (e.g., surfaces separated by a hybrid board carrying each of the temperature sensors). In this example, each temperature sensor may be mounted on opposing sides of the hybrid board such that one sensor senses temperature on one side of the hybrid board and the other sensor senses temperature on the opposite side off the hybrid board.

Each temperature sensor may sense temperatures simultaneously such that system 10 may process multiple temperatures at the same time. Alternatively, one or more temperature sensors may be selectively enabled by one or more processors. This selective temperature sensing may reduce power consumption from unnecessary temperature sensors. In addition, selective temperature sensing may reduce power consumption and/or processing speed needed to process signals from unneeded temperature sensors. In one example, each of the plurality of IR temperature sensors may include a shutter that opens to detect IR energy and closes to prevent IR energy detection. The processor may select to sense the temperature of a first portion of the device with a first temperature sensor instead of a second portion of the device with a second temperature sensor. Responsive to the selection, the processor may control a first shutter of the first temperature sensor to open and control a second shutter of the second temperature sensor to close. Alternatively or additionally, the processor may selectively send power to desired temperature sensors to sense the temperature of a portion of the device associated with the selected portion.

In some examples, a phase change material may be used to facilitate temperature sensing of one or more components of the device. The phase change material may be disposed on the surface of a component from which temperature is to be sensed. The component may be a housing of the device, a coil that transfers energy to rechargeable power source 18 during charging (e.g., a primary or secondary coil), or any other component within the device. The phase change material may provide multiple advantages to sensing the desired temperature. The phase change material may function as a heat sink to reduce the temperature of the component to which the phase change material is in contact. In addition, the phase change material may distribute temperatures across the component and reduce the frequency and/or intensities of temperature variation (e.g., hot spots). In some examples, the phase change material may even facilitate temperature detection from a material with a difficult to detect emissivity. In some examples, the phase change material may be disposed on only a portion of a component. In other examples, the phase change material may be disposed over the entire surface of the component. The phase change material may be encapsulated by a membrane, embedded in a woven fabric, or otherwise disposed in at least partial contact with a surface of the component.

System 10 may control the charging of rechargeable power source 18 using one or more techniques. Using the sensed temperature, a processor may compare the sensed temperature to a threshold temperature. The sensed temperature may be from a temperature sensor located within IMD 14 and/or charging device 22. The threshold temperature may be a value stored by a memory. The threshold temperature may be selected based on tissue models, patient history, or any other information that may be used to determine when a charging session should be modified. The processor may then determine when the sensed temperature exceeds the threshold temperature. When the sensed temperature exceeds the threshold temperature, the processor may control charging of rechargeable power source 18 by adjusting a power level used to charge rechargeable power source 18. In other words, the processor may reduce the power level when the temperature threshold is exceeded, turn the power off for a predetermined period of time before the power is again provided (e.g., cycle the power on and off) or even terminate the charging session. Reducing the power level may reduce the energy used to charge rechargeable power source 18 and/or the rate at which rechargeable power source 18 is recharged.

When sensing a temperature of a component of IMD 14, a processor of IMD may merely transmit the calculated temperature or data representative of the temperature to charging device 22. A processor of charging device 22 may then determine how to control the charging session. Alternatively, the processor of IMD 14 may determine how to control the charging session and transmit a respective command to charging device 22.

Charging device 22 may thus charge rechargeable power source 18 using one or more power levels or cycle times in some examples. In one example, charging device 22 may select a high power level when first starting a charging session. Charging device 22 may then select a low power level, relative to the high power level, in response to one or more temperature sensors exceeding a threshold. In this manner, the high power level may charge rechargeable power source 18 at a high rate to reduce charging time while increasing the temperature of IMD 14. Charging device 22 may select the low power level to charge rechargeable power source 18 at a slower rate to reduce the temperature of IMD 14. The low power level may be sufficiently minimal so that any increase in temperature of IMD 14 may have minimal or no effect on surrounding tissue.

A high power level and a low power level may be subjective and relative to the charging power that charging device 22 is capable of generating and transmitting to IMD 14. In some cases, the high power level may be the maximum power that charging device 22 can generate. This high power level may be referred to as a "boost" or "accelerated" charging level because of the high rate of charge induced in rechargeable power source 18. This high rate of charge may minimize the amount of time patient 12 needs to recharge rechargeable power source 18. By monitoring the temperature of one or more portions of charging head 26 and/or IMD 14, charging device 22 may charge rechargeable power source 18 with the high power level for a longer period of time without damaging tissue surrounding IMD 14.

In one example, the high power level may be approximately 2.5 Watts and the low power level may be approximately 1.0 Watt (W). Of course other power levels and ranges may be selected for use, with such levels falling either within the above-described range or outside of this range. For instance, a low power level may be much lower than 1.0 Watt in an example wherein there is good coupling between primary and second coils and wherein recharge is to be conducted relatively slowly. An example charge current level may be approximately 100 milliamps (mA) for the high power level and approximately 60 mA for the low power level. An example primary coil voltage and current for a high power may be approximately 450 V and approximately 800 mA, respectively, and an example primary coil voltage and current for a low power level may be approximately 250 V and approximately 500 mA. These values are merely examples, and other examples may include higher or lower values in accordance with the techniques described herein. In additional more than two levels may be defined (e.g., low, one or more intermediate levels, and a high level) to control charging.

In some cases, charging device 22 may cycle the driving of the primary coil. For instance, charging device 22 may drive the coil during a first period of time, and may discontinue driving the coil for a second period of time following the first period of time. This may be repeated multiple times, with the first and second time periods being selected to control an overall transmission of power (and hence heat dissipation.)

In some examples, IMD 14 may directly adjust the power level for charging (e.g., limit the charge current) instead of relying on a change in power level at charging device 22. For example, as IMD 14 receives an alternating charging current, IMD 14 may employ a circuit that may change from full-wave rectification to half-wave rectification to reduce the charge rate and temperature of IMD 14 during charging. In other words, IMD 14 may utilize half-wave rectification as a means to reduce the electrical current delivered to rechargeable power supply 18 instead of reducing the overall power received by IMD 14. Alternatively, IMD 14 may employ other mechanisms such as current and/or voltage limiters that may limit the charging rate of rechargeable power supply 18.

In other examples, a processor of charging device 22 and/or IMD 14 may perform actions other than changing a power level for charging in response to temperature changes. For example, charging device 22 may instruct a user to replace a phase change material cartridge attached to charging head 26 of charging device 22. The phase change material cartridge may act as a heat sink and increase the amount of time charging device 22 can charge rechargeable power source 18 at a high power level. In one example, a processor of charging device 22 may calculate a temperature change rate from the multiple sensed temperatures when rechargeable power source 18 is charging. The temperature change rate may be representative of how fast the temperature of charging head 26 is changing. As described above, charging head 26 may include a primary coil that transfers power wirelessly to a secondary coil within IMD 14. The processor may then determine when the temperature change rate increases subsequent to the temperature change rate decreasing during the charging. In response to determining that the temperature change rate has increased, the processor may control a user interface to present a notification that instructs a user to replace a phase change material cartridge thermally coupled to the device.

In other words, the processor may identify inflection points as the temperature changes. Once the temperature of the phase change material reaches the melting point of the material, additional heat is transferred into changing the phase of the material instead of raising the temperature. However, after the material has changed phase, the sensed temperature may again increase. Upon this detected increase in temperature, charging device 22 may determine that the phase change material is no longer capable of suppressing the temperature increases of charging head 26. Since the cartridge may be replaceable, charging device 22 may present a visual, audio, or tactile notification that instructs the user to replace the cartridge. If the user does not replace the cartridge prior to the temperate exceeding a threshold, charging device 22 may then reduce the power level of charging or terminate the charging session.

As described herein, a non-thermally coupled temperature sensor may be used to sense a temperature of a portion of IMD 14 (including rechargeable power source 18), charging head 26, and/or housing 24. A processor that controls an aspect of the charging session may be housed by IMD 14, charging head 26, or housing 24. In this manner, a processor configured to perform some or all of the functions described herein may be housed together with a temperature sensor or separate from the temperature sensor.

Although an implantable rechargeable power source 18 is generally described herein, techniques of this disclosure may also be applicable to a rechargeable power source 18 that is not implanted. For example, rechargeable power source 18 may be external to the skin of patient 12 and in physical contact with the skin. Therefore, charging device 22 may control the charging of rechargeable power source 18 with temperature sensed within charging head 26 or IMD 14 even when the power source is external to patient 12.

Figure 2:
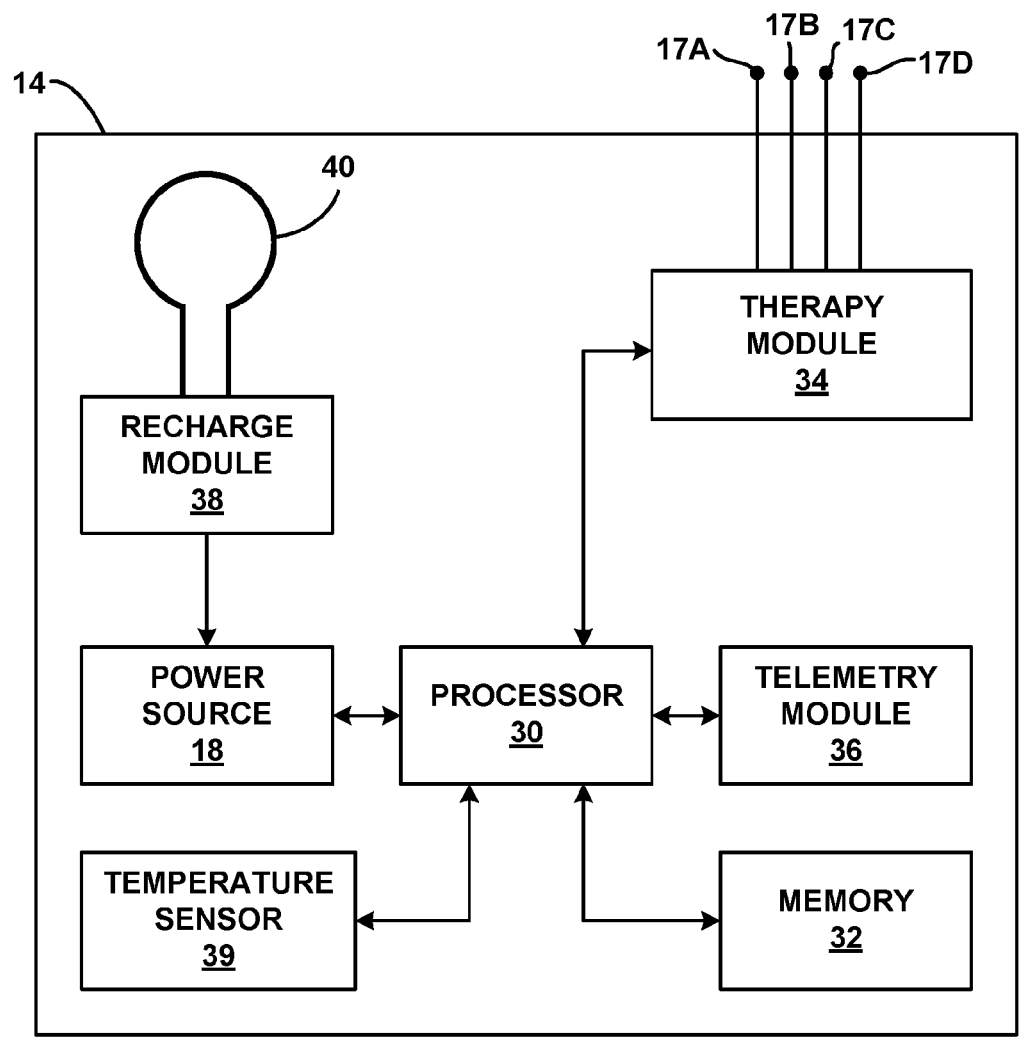
FIG. 2 is a block diagram of the example IMD of FIG. 1.

FIG. 2 is a block diagram illustrating example components of IMD 14. In the example of FIG. 2, IMD 14 includes temperature sensor 39, coil 40, processor 30, therapy module 34, recharge module 38, memory 32, telemetry module 36, and rechargeable power source 18. In other examples, IMD 14 may include a greater or a fewer number of components. For example, in some examples, IMD 14 may not include temperature sensor 39.

In general, IMD 14 may comprise any suitable arrangement of hardware, alone or in combination with software and/or firmware, to perform the various techniques described herein attributed to IMD 14 and processor 30. In various examples, IMD 14 may include one or more processors 30, such as one or more microprocessors, digital signal processors (DSPs), application specific integrated circuits (ASICs), field programmable gate arrays (FPGAs), or any other equivalent integrated or discrete logic circuitry, as well as any combinations of such components. IMD 14 also, in various examples, may include a memory 32, such as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them. Moreover, although processor 30, therapy module 34, recharge module 38, and telemetry module 36 are described as separate modules, in some examples, processor 30, therapy module 34, recharge module 38, and telemetry module 36 are functionally integrated. In some examples, processor 30, therapy module 34, recharge module 38, and telemetry module 36 correspond to individual hardware units, such as ASICs, DSPs, FPGAs, or other hardware units.

Memory 32 may store therapy programs or other instructions that specify therapy parameter values for the therapy provided by therapy module 34 and IMD 14. In some examples, memory 32 may also store temperature data from temperature sensor 39, instructions for recharging rechargeable power source 18, thresholds, instructions for communication between IMD 14 and charging device 22, or any other instructions required to perform tasks attributed to IMD 14. Memory 32 may be configured to store instructions for communication with and/or controlling one or more temperature sensors 39. As described herein, the non-thermally coupled temperature sensor 39 may be an IR sensor, a phosphor temperature sensor, or any other non-contact sensor or sensor (whether or not contact) that senses temperature by means other than thermal coupling.

Generally, therapy module 34 may generate and deliver electrical stimulation under the control of processor 30. In some examples, processor 30 controls therapy module 34 by accessing memory 32 to selectively access and load at least one of the stimulation programs to therapy module 34. For example, in operation, processor 30 may access memory 32 to load one of the stimulation programs to therapy module 34. In such examples, relevant stimulation parameters may include a voltage amplitude, a current amplitude, a pulse rate, a pulse width, a duty cycle, or the combination of electrodes 17A, 17B, 17C, and 17D that therapy module 34 uses to deliver the electrical stimulation signal. Therapy module 34 may be configured to generate and deliver electrical stimulation therapy via one or more of electrodes 17A, 17B, 17C, and 17D of lead 16. Alternatively, or additionally, therapy module 34 may be configured to provide different therapy to patient 12. For example, therapy module 34 may be configured to deliver drug delivery therapy via a catheter. These and other therapies may be provided by IMD 14.

IMD also includes components to receive power from charging device 22 to recharge rechargeable power source 18 when rechargeable power source 18 has been at least partially depleted. As shown in FIG. 2, IMD 14 includes secondary coil 40 and recharge module 38 coupled to rechargeable power source 18. Recharge module 38 may be configured to charge rechargeable power source 18 with the selected power level determined by either processor 30 or charging device 22. Recharge module 38 may include any of a variety of charging and/or control circuitry configured to process or convert current induced in coil 40 into charging current to charge power source 18. Although processor 30 may provide some commands to recharge module 38, in some examples, processor 30 may not need to control any aspect of recharging.

Secondary coil 40 may include a coil of wire or other device capable of inductive coupling with a primary coil disposed external to patient 12. Although secondary coil 40 is illustrated as a simple loop of in FIG. 2, secondary coil 40 may include multiple turns of conductive wire. Secondary coil 40 may include a winding of wire configured such that an electrical current can be induced within secondary coil 40 from a magnetic field. The induced electrical current may then be used to recharge rechargeable power source 18. In this manner, the electrical current may be induced in secondary coil 40 associated with rechargeable power source 18. The induction may be caused by electrical current generated in the primary coil of charging device 22, where the level of the current may be based on the selected power level. The coupling between secondary coil 40 and the primary coil of charging device 22 may be dependent upon the alignment of the two coils. Generally, the coupling efficiency increases when the two coils share a common axis and are in close proximity to each other. Charging device 22 and/or IMD 14 may provide one or more audible tones or visual indications of the alignment.

Although inductive coupling is generally described as the method for recharging rechargeable power source 18, other wireless energy transfer techniques may alternatively be used. Any of these techniques may generate heat in IMD 14 such that the charging process can be controlled by matching the sensed temperature to one or more thresholds, modeling tissue temperatures based on the sensed temperature, or using a calculated cumulative thermal dose as feedback.

Recharge module 38 may include one or more circuits that process, filter, convert and/or transform the electrical signal induced in secondary coil to an electrical signal capable of recharging rechargeable power source 18. For example, in alternating current induction, recharge module 38 may include a half-wave rectifier circuit and/or a full-wave rectifier circuit configured to convert alternating current from the induction to a direct current for rechargeable power source 18. The full-wave rectifier circuit may be more efficient at converting the induced energy for rechargeable power source 18. However, a half-wave rectifier circuit may be used to store energy in rechargeable power source 18 at a slower rate. In some examples, recharge module 38 may include both a full-wave rectifier circuit and a half-wave rectifier circuit such that recharge module 38 may switch between each circuit to control the charging rate of rechargeable power source 18 and temperature of IMD 14.

Rechargeable power source 18 may include one or more capacitors, batteries, and/or other energy storage devices. Rechargeable power source 18 may deliver operating power to the components of IMD 14. In some examples, rechargeable power source 18 may include a power generation circuit to produce the operating power. Rechargeable power source 18 may be configured to operate through hundreds or thousands of discharge and recharge cycles. Rechargeable power source 18 may also be configured to provide operational power to IMD 14 during the recharge process. In some examples, rechargeable power source 18 may be constructed with materials to reduce the amount of heat generated during charging. In other examples, IMD 14 may be constructed of materials that may help dissipate generated heat at rechargeable power source 18, recharge module 38, and/or secondary coil 40 over a larger surface area of the housing of IMD 14.

Although rechargeable power source 18, recharge module 38, and secondary coil 40 are shown as contained within the housing of IMD 14, in alternative implementations, at least one of these components may be disposed outside of the housing. For example, in some implementations, secondary coil 40 may be disposed outside of the housing of IMD 14 to facilitate better coupling between secondary coil 40 and the primary coil of charging device 22. These different configurations of IMD 14 components may allow IMD 14 to be implanted in different anatomical spaces or facilitate better inductive coupling alignment between the primary and secondary coils.

IMD 14 may also include temperature sensor 39. Temperature sensor 39 may include one or more non-thermally coupled temperature sensors configured to measure the temperature of respective portions of IMD 14. As described herein, a non-thermally coupled temperature sensor is not thermally coupled to, and may not be directly attached to, the portion of the device from which temperature is to be measured. In one instance, the temperature sensor is not directly attached to the portion of the device. In other words, temperature measurement is not performed through direct contact or physical contact between the temperature sensor and the target portion to be measured. Although the temperature sensor may be physically attached to the target portion or target surface through one or more structures, any thermal conduction that may occur between the target portion and the sensor is not used to measure the temperature of the target portion.

Temperature sensor 39 may be oriented to measure the temperature of a component, surface or structure (e.g., secondary coil 40, power source 19, recharge module 38, or the housing) of IMD 14. Temperature sensor 39 may be disposed internal of the housing of IMD 14 or otherwise disposed relative to the external portion of housing (e.g., tethered to an external surface of housing via an appendage cord). As described herein, temperature sensor 39 may be used to use non-contact temperature measurements of IMD 14 to infer the temperature of tissue surrounding and/or contacting the housing of IMD 14. Processor 30, or charging device 22, may use this temperature measurement as the tissue temperature feedback to control the power levels or charge times (e.g., cycle times) used during the charging session. Although a single temperature sensor may be adequate, multiple temperature sensors may provide more specific temperature readings of separate components or different areas of the housing. Although processor 30 may continually measure temperature using temperature sensor 39, processor 30 may conserve energy by only measuring temperature during recharge sessions. Further, temperature may be sampled at a rate necessary to effectively control the charging session, but the sampling rate may be reduced to conserve power as appropriate.

Processor 30 may also control the exchange of information with charging device 22 and/or an external programmer using telemetry module 36. Telemetry module 36 may be configured for wireless communication using radio frequency protocols or inductive communication protocols. Telemetry module 36 may include one or more antennas configured to communicate with charging device 22, for example. Processor 30 may transmit operational information and receive therapy programs or therapy parameter adjustments via telemetry module 36. Also, in some examples, IMD 14 may communicate with other implanted devices, such as stimulators, control devices, or sensors, via telemetry module 36. In addition, telemetry module 36 may be configured to transmit the measured tissue temperatures from temperature sensor 39, for example.

In other examples, processor 30 may transmit additional information to charging device 22 related to the operation of rechargeable power source 18. For example, processor 30 may use telemetry module 36 to transmit indications that rechargeable power source 18 is completely charged, rechargeable power source 18 is fully discharged, or any other charge status of rechargeable power source 18. Processor 30 may also transmit information to charging device 22 that indicates any problems or errors with rechargeable power source 18 that may prevent rechargeable power source 18 from providing operational power to the components of IMD 14.

Figure 3:
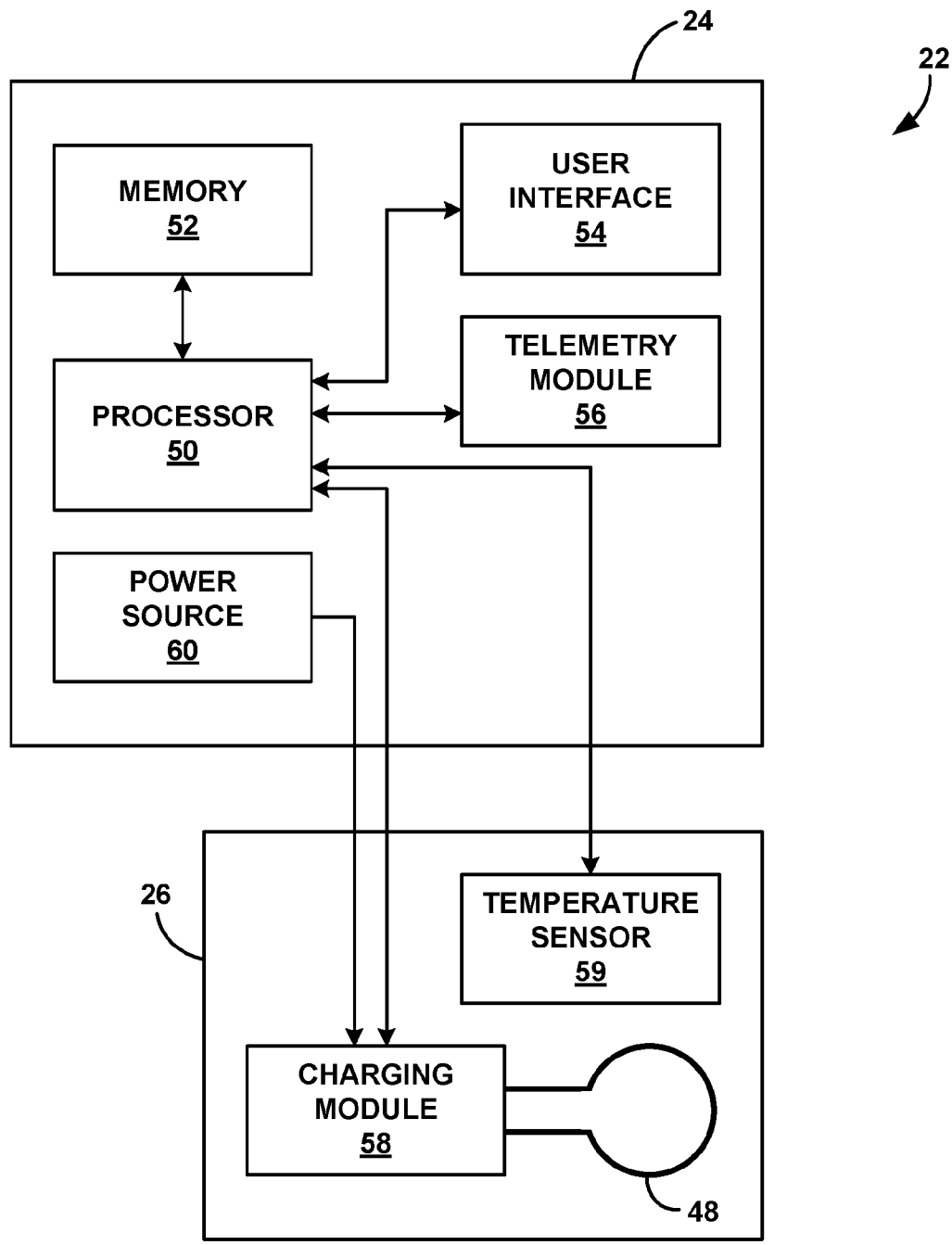
FIG. 3 is a block diagram of the example external charging device of FIG. 1.

FIG. 3 is a block diagram of the example external charging device 22. While charging device 22 may generally be described as a hand-held device, charging device 22 may be a larger portable device or a more stationary device. In addition, in other examples, charging device 22 may be included as part of an external programmer or include functionality of an external programmer. In addition, charging device 22 may be configured to communicate with an external programmer. As shown in FIG. 3, charging device 22 includes two separate components. Housing 24 encloses components such as a processor 50, memory 52, user interface 54, telemetry module 56, and power source 60. Charging head 26 may include power module 58, temperature sensor 59, and coil 48. A different partitioning of components is also possible, such as including one or more of the foregoing components within a module carried by the cord of charging device 22.

A separate charging head 26 may facilitate optimal positioning of coil 48 over coil 40 of IMD 14. However, charging module 58 and/or coil 48 may be integrated within housing 24 in other examples. Memory 52 may store instructions that, when executed by processor 50, cause processor 50 and external charging device 22 to provide the functionality ascribed to external charging device 22 throughout this disclosure.

External charging device 22 may also include one or more non-thermally coupled temperature sensors 59, similar to temperature sensor 39 of FIG. 2. Temperature sensor 59 may be disposed within charging head 26 and/or housing 24. For example, charging head 26 may include one or more non-thermally coupled temperature sensors positioned and configured to sense the temperature of coil 48 and/or a surface of the housing of charging head 26. In some examples, charging device 22 may not include temperature sensor 59.

In general, charging device 22 comprises any suitable arrangement of hardware, alone or in combination with software and/or firmware, to perform the techniques attributed to charging device 22, and processor 50, user interface 54, telemetry module 56, and charging module 58 of charging device 22. In various examples, charging device 22 may include one or more processors, such as one or more microprocessors, DSPs, ASICs, FPGAs, or any other equivalent integrated or discrete logic circuitry, as well as any combinations of such components. Charging device 22 also, in various examples, may include a memory 52, such as RAM, ROM, PROM, EPROM, EEPROM, flash memory, a hard disk, a CD-ROM, comprising executable instructions for causing the one or more processors to perform the actions attributed to them. Moreover, although processor 50 and telemetry module 56 are described as separate modules, in some examples, processor 50 and telemetry module 56 are functionally integrated. In some examples, processor 50 and telemetry module 56 and charging module 58 correspond to individual hardware units, such as ASICs, DSPs, FPGAs, or other hardware units.

Memory 52 may store instructions that, when executed by processor 50, cause processor 50 and charging device 22 to provide the functionality ascribed to charging device 22 throughout this disclosure. For example memory 52 may include instructions that cause processor 50 to control the power level used to charge IMD 14 in response to the sensed temperatures, communicate with IMD 14, or instructions for any other functionality. In addition, memory 52 may include a record of selected power levels, sensed temperatures, or any other data related to charging rechargeable power source 18. Processor 50 may, when requested, transmit any of this stored data in memory 52 to another computing device for review or further processing.

User interface 54 may include a button or keypad, lights, a speaker for voice commands, a display, such as a liquid crystal (LCD), light-emitting diode (LED), or cathode ray tube (CRT). In some examples the display may be a touch screen. As discussed in this disclosure, processor 50 may present and receive information relating to the charging of rechargeable power source 18 via user interface 54. For example, user interface 54 may indicate when charging is occurring, quality of the alignment between coils 40 and 48, the selected power level, current charge level of rechargeable power source 18, duration of the current recharge session, anticipated remaining time of the charging session, sensed temperatures, instructions for changing a phase change material cartridge of charging head 26, or any other information. Processor 50 may receive some of the information displayed on user interface 54 from IMD 14 in some examples.

User interface 54 may also receive user input via user interface 54. The input may be, for example, in the form of pressing a button on a keypad or selecting an icon from a touch screen. The input may request starting or stopping a recharge session, a desired level of charging, or one or more statistics related to charging rechargeable power source 18 (e.g., the cumulative thermal dose). In this manner, user interface 54 may allow the user to view information related to the charging of rechargeable power source 18 and/or receive charging commands.

Charging device 22 also includes components to transmit power to recharge rechargeable power source 18 associated with IMD 14. As shown in FIG. 3, charging device 22 includes primary coil 48 and charging module 58 coupled to power source 60. Charging module 58 may be configured to generate an electrical current in primary coil 48 from voltage stored in power source 60. Although primary coil 48 is illustrated as a simple loop in FIG. 3, primary coil 48 may include multiple turns of wire. Charging module 58 may generate the electrical current according to a power level selected by processor 50 based on the sensed temperature or temperatures received from IMD 14 or a temperature sensor within charging device 22. As described herein, processor 50 may select a high power level, low power level, or a variety of different power levels to control the rate of recharge in rechargeable power source 18 and the temperature of IMD 14. In some examples, processor 50 may control charging module 58 based on a power level selected by processor 30 of IMD 14. The sensed temperature used as feedback for control of the recharge power level may be from a temperature sensed by a temperature sensor within IMD 14 and/or charging device 22. Although processor 50 may control the power level used for charging rechargeable power source 18, charging module 58 may include one or more processors configured to partially or fully control the power level based on the sensed temperatures.

Primary coil 48 may include a coil of wire, e.g., having multiple turns, or other device capable of inductive coupling with a secondary coil 40 disposed within patient 12. Primary coil 48 may include a winding of wire configured such that an electrical current generated within primary coil 48 can produce a magnetic field configured to induce an electrical current within secondary coil 40. The induced electrical current may then be used to recharge rechargeable power source 18. In this manner, the electrical current may be induced in secondary coil 40 associated with rechargeable power source 18. The coupling efficiency between secondary coil 40 and primary coil 48 of charging device 22 may be dependent upon the alignment of the two coils. Generally, the coupling efficiency increases when the two coils share a common axis and are in close proximity to each other. User interface 54 of charging device 22 may provide one or more audible tones or visual indications of the alignment.

Charging module 58 may include one or more circuits that generate an electrical signal, and an electrical current, within primary coil 48. Charging module 58 may generate an alternating current of specified amplitude and frequency in some examples. In other examples, charging module 58 may generate a direct current. In any case, charging module 58 may be capable of generating electrical signals, and subsequent magnetic fields, to transmit various levels of power to IMD 14. In this manner charging module 58 may be configured to charge rechargeable power source 18 of IMD 14 with the selected power level.

The power level that charging module 58 selects for charging may be used to vary one or more parameters of the electrical signal generated for coil 48. For example, the selected power level may specify wattage, electrical current of primary coil 48 or secondary coil 40, current amplitude, voltage amplitude, pulse rate, pulse width, a cycling rate that determines when the primary coil is driven, or any other parameter that may be used to modulate the power transmitted from coil 48. In this manner, each power level may include a specific parameter set that specifies the signal for each power level. Changing from one power level to another power level (e.g., a high power level to a lower power level) may include adjusting one or more parameters. For instance, at a high power level, the primary coil may be substantially continuously driven, whereas at a lower power level, the primary coil may be intermittently driven such that periodically the coil is not driven for a predetermined time to control heat dissipation. The parameters of each power level may be selected based on hardware characteristics of charging device 22 and/or IMD 14.

Power source 60 may deliver operating power to the components of charging device 22. Power source 60 may also deliver the operating power to drive primary coil 48 during the charging process. Power source 60 may include a battery and a power generation circuit to produce the operating power. In some examples, a battery of power source 60 may be rechargeable to allow extended portable operation. In other examples, power source 60 may draw power from a wired voltage source such as a consumer or commercial power outlet.

Charging device 22 may include one or more non-thermally coupled temperature sensor 59 (e.g., similar to temperature sensor 39 of IMD 14) for sensing the temperature of a portion of the device. For example, temperature sensor 59 may be disposed within charging head 26 and oriented to sense the temperature of the housing of charging head 26. In another example, temperature sensor 59 may be disposed within charging head 26 and oriented to sense the temperature of charging module 58 and/or coil 48. In other examples, charging device 22 may include multiple temperature sensors 59 each oriented to any of these portions of device to manage the temperature of the device during charging sessions.

Telemetry module 56 supports wireless communication between IMD 14 and charging device 22 under the control of processor 50. Telemetry module 56 may also be configured to communicate with another computing device via wireless communication techniques, or direct communication through a wired connection. In some examples, telemetry module 56 may be substantially similar to telemetry module 36 of IMD 14 described herein, providing wireless communication via an RF or proximal inductive medium. In some examples, telemetry module 56 may include an antenna, which may take on a variety of forms, such as an internal or external antenna. Although telemetry modules 56 and 36 may each include dedicated antennae, telemetry modules 56 and 36 may instead, or additionally, be configured to utilize inductive coupling from coils 40 and 48 to transfer data.

Examples of local wireless communication techniques that may be employed to facilitate communication between charging device 22 and IMD 14 include radio frequency and/or inductive communication according to any of a variety of standard or proprietary telemetry protocols, or according to other telemetry protocols such as the IEEE 802.11x or Bluetooth specification sets. In this manner, other external devices may be capable of communicating with charging device 22 without needing to establish a secure wireless connection. As described herein, telemetry module 56 may be configured to receive a signal or data representative of a measured tissue temperature from IMD 14. The tissue temperature may be indirectly measured by measuring the temperature of the internal surface of the IMD housing adjacent to rechargeable power source 18. In some examples, multiple temperature readings by IMD 14 may be averaged or otherwise used to produce a single temperature value that is transmitted to charging device 22. The sensed temperature may be sampled and/or transmitted by IMD 14 (and received by charging device 22) at different rates, e.g., on the order of microseconds, milliseconds, seconds, minutes, or even hours. Processor 50 may then use the received temperature to control charging of rechargeable power source 18 (e.g., control the charging level used to recharge power source 18).

Figure 4A:
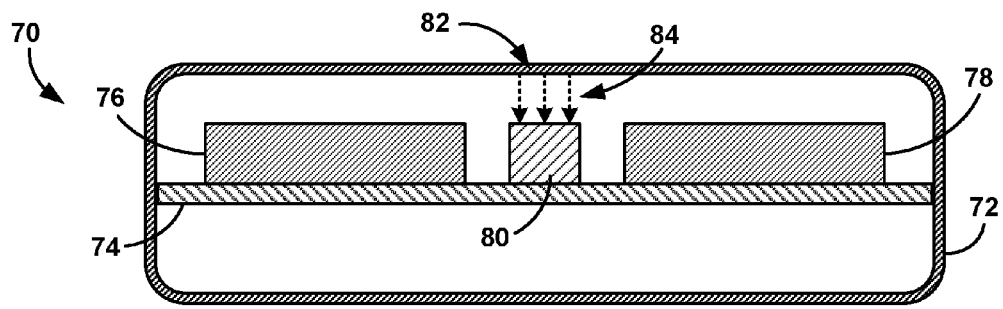
FIGS. 4A-4C are conceptual diagrams illustrating example temperature sensors disposed within respective IMDs.
Figure 4B:
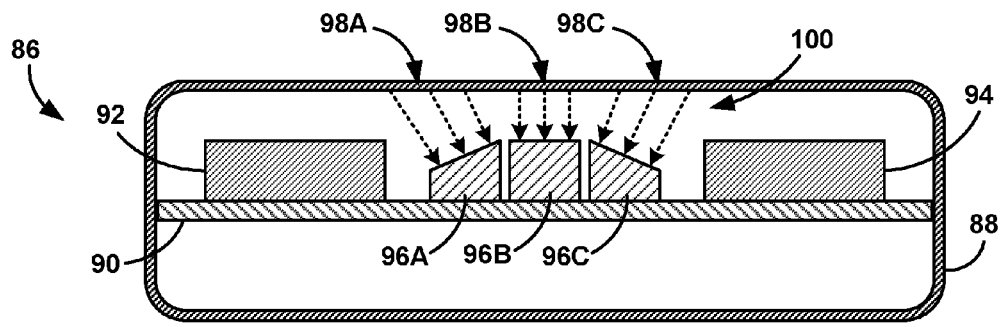
Figure 4C:
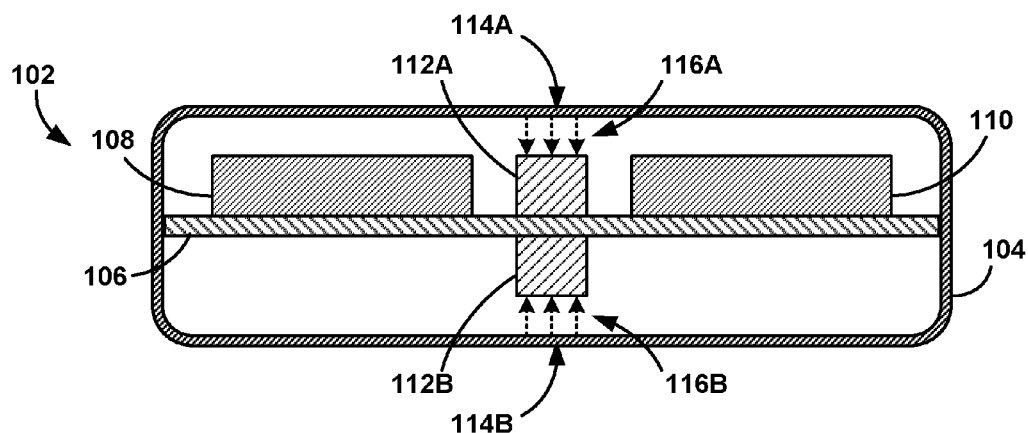

FIGS. 4A-4C are conceptual cross-sectional diagrams illustrating example temperature sensors disposed 80, 96, and 112 within respective IMDs 70, 86, and 102. IMDs 70, 86, and 102 are examples of IMD 14, and each of temperature sensors 80, 96, and 112 are examples of non-thermally coupled temperature sensor 39. Although temperature sensors may be described with respect to a specific type of device such as an IMD, the temperature sensors may alternatively be disposed within a different type of device such as charging device 22 (e.g., within housing 24 or charging head 26). IR temperature sensors are provided as an example sensor in FIGS. 4A-4C. The IMDs described herein are generally shown with rectangular cross-sections. However, non-thermally coupled temperature sensors may be disposed within IMDs or any other devices of any shapes, dimensions, or sizes.

As shown in FIG. 4A, IMD 70 includes housing 72 that encloses hybrid board 74, electronics 76 and 78, and temperature sensor 80. Hybrid board 74 may be mounted or secured within housing 72. Electronics 76 and 78 may include various components such as a processor and memory and associated circuitry. Although not shown in FIG. 4A, a secondary coil and rechargeable power source may also be disposed within housing 72. Temperature sensor 80 may be mounted onto a surface of hybrid board 74.

Temperature sensor 80 may be an infrared temperature sensor oriented in a specific manner to detect infrared radiation emitted from a desired location of housing 72. Portion 82 may be an area of housing 72 from which the temperature is to be sensed. Portion 82 may emit IR energy 84 as a function of the temperature of portion 82. As IR energy 84 is emitted from portion 82, temperature sensor 80 may detect at least some of IR energy 84 and output a signal representative of the intensity of IR energy 84. Although IR energy 84 may be emitted in several directions from portion 82, temperature sensor 80 may only detect the IR energy directly transmitted from portion 82.

IR energy 84 may travel through a vacuum, a gas, or other medium separating temperature sensor 80 from portion 82. In some examples, temperature sensor 80 may be disposed in close proximity to portion 82. However, temperature sensor 80 may sense the temperature of portion 82 via IR energy 84 instead of heat conducted between portion 82 and temperature sensor 80. Instead of being oriented toward portion 82, temperature sensor 80 may detect IR energy from other portions of housing 72 or even other components (e.g., a component of electrodes 78).

As shown in FIG. 4B, IMD 86 includes housing 88 that encloses hybrid board 90, electronics 92 and 94, and temperature sensors 96A, 96B, and 96C (collectively "temperature sensors 96"). Hybrid board 90 may be mounted or secured within housing 88. Temperature sensors 96 may be IR temperature sensors oriented in a specific manner to detect infrared radiation emitted from specific locations of housing 88. Portions 98A, 98B, and 98C (collectively "portions 98") are respective areas of housing 88 from which the temperature is to be sensed. Different portions 98 may be sensed for temperature differences due to variations in temperature caused by components within housing 88 or external influences. Each of portions 98 may emit IR energy 100 as a function of the temperature of the respective portions 98. However, each of temperature sensors 96 are oriented to receive the portion of IR energy 100 emitted from the respective portion 98. Therefore, temperature sensors 96 may sense variations in temperature between the different portions 98.

The variations in temperature between portions 98 may be used to generate an average temperature of housing 88, a weighted average, or identify one or more hot spots of housing 88. In other examples, the multiple temperature measurements of portions 98 may be used to generate a temperature gradient that models the temperature at different locations of housing 88. Charging device 22 may then control power levels for charging based on temperature of one or more hot spots, based on the detected gradient, or based on another aspect of the temperature readings to prevent sensitive tissues, for example, from being exposed to undesirable temperatures.

Temperature sensors 96 are all disposed on the same side of hybrid board 90. Although temperature sensors 96A and 96C are oriented at non-orthogonal angles with respect to housing 88, other sensors may be positioned at orthogonal angles in other examples. In addition, multiple temperature sensors may be disposed at any location, and with any orientation, within housing 88. For example, each temperature sensor 96 may be mounted at a location on hybrid board 90 that would be closest to the desired portion of housing 88 for temperature sensing. In this manner, temperature sensors may be selected to be positioned at any location within housing 88.

As shown in FIG. 4C, in another example, IMD 102 includes housing 104 that encloses hybrid board 106, electronics 108 and 110, and temperature sensors 112A and 112B (collectively "temperature sensors 112"). Hybrid board 106 may be mounted or secured within housing 104. Temperature sensors 112 may be IR temperature sensors oriented in a specific manner to detect infrared radiation emitted from specific locations of housing 104. In the example of IMD 102, temperature sensors 112 may be positioned to sense the temperature of opposing surfaces of housing 104. In other words, portions 114A and 114B (collectively "portions 114") are generally opposite each other. In some examples, sensing the temperature on opposing sides of IMD 102 may be beneficial if IMD 102 becomes flipped within the tissue pocket containing IMD 102 within patient 12. In other words, IMD 102 may be configured to determine that a flip has occurred and/or measure the temperature of a desired surface of housing 104 regardless of if IMD 102 has flipped within patient 12.

Since hybrid board 106 separates portions 114A and 114B, temperature sensors 112A and 112B may be mounted on opposing surfaces of hybrid board 106. Each of temperature sensors 112 may thus be oriented to receive IR energy 116A and 116B from respective portions 114A and 114B. In other examples, temperature sensors 112 may be mounted on the same side of hybrid board 106 and still capable of detecting IR energy 116A and 116B. For example, a hole or window may be formed in hybrid board 106 such that the IR energy can pass through hybrid board and to the appropriate temperature sensor. By positioning multiple non-thermally coupled temperature sensors within IMD 102, the temperature at different locations of housing 104 or at different locations internal to IMD may be sensed and used to control the charging of rechargeable power source 18. For example, external charging device 22 may control the power level used to recharge power source 18 based on the measured temperatures within IMD 102.

Figure 5A:
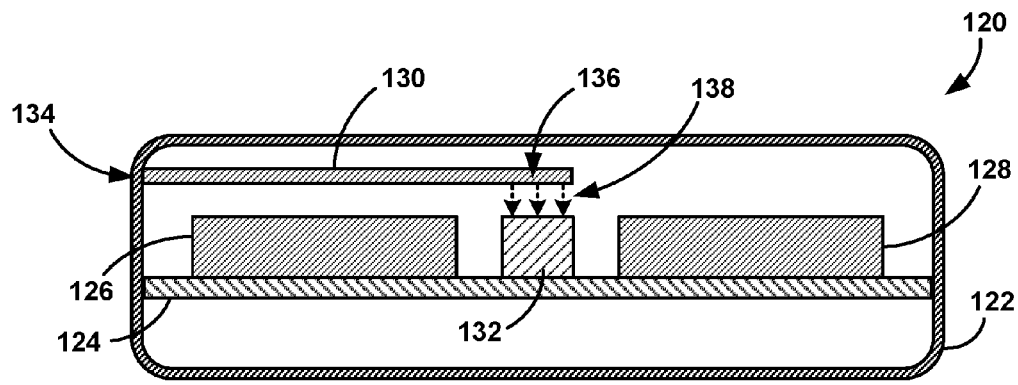
FIGS. 5A and 5B are conceptual diagrams illustrating example temperature sensors and structures that transfer energy associated with a desired portion of respective IMDs.
Figure 5B:
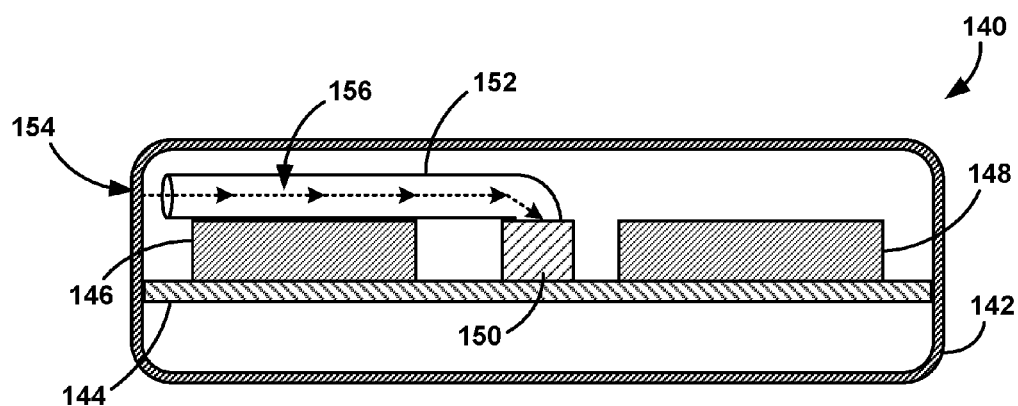

FIGS. 5A and 5B are conceptual cross-sectional diagrams illustrating example temperature sensor 132 and 150 and respective structures that transfer energy associated with a desired portion of an IMD. IMDs 120 and 140 are examples of IMD 14, and each of temperature sensors 132 and 150 are examples of non-thermally coupled temperature sensor 39. IR temperature sensors are provided as an example sensor in FIGS. 5A and 5B, and may be similar to temperature sensor 80 of FIG. 4A.

As shown in FIG. 5A, IMD 120 includes housing 122 that encloses hybrid board 124, electronics 126 and 128, and temperature sensor 132. Hybrid board 124 may be mounted or secured within housing 122. Electronics 126 and 128 may include various components such as a processor and memory. Although not shown in FIG. 5A, a secondary coil and rechargeable power source may also be disposed within housing 122. Temperature sensor 132 may be mounted onto a surface of hybrid board 124.

In addition to temperature sensor 132, heat pipe 130 may be disposed within housing 122 to transfer energy from portion 134 to temperature sensor 132. In some examples, the desired area from which temperature is to be sensed may not be within line-of-sight from temperature sensor 132. However, heat pipe 130 (or another energy transfer structure) may transfer the energy from the desired surface or object to temperature sensor 132. In the example of FIG. 5A, heat pipe 132 may be configured to be thermally coupled to portion 134 of housing 122. Heat pipe 132 may be a thermally conductive such that the temperature of portion 134 is approximately similar to any location along heat pipe 130. Since portion 136 of heat pipe 136 may also emit IR energy 138, temperature sensor 132 may detect IR energy 138 as a representation of the temperature of portion 134 of housing 122. In some cases, a function (e.g., a mathematical function) may be employed to convert the heat detected by heat pipe 136 into a representation of the heat of portion 134 of housing. For instance, this may involve multiplying the detected heat by a constant that takes into account effects caused by heat pipe.

Although only one heat pipe 130 is provided, IMD 120 may include two or more heat pipes to transfer energy from multiple portions within IMD 120. Heat pipe 132 may be constructed of a solid structure, hollow structure, or any other configuration in which the material of heat pipe 132 conducts heat energy from the target surface (e.g., portion 134) to temperature sensor 150.

Temperature sensor 132 may be an infrared temperature sensor oriented in a specific manner to detect IR energy 138 from heat pipe 130. Portion 136 may emit IR energy 138 as a function of the temperature of portion 136 and portion 134. As IR energy 138 is emitted from portion 136, temperature sensor 132 may detect at least some of IR energy 138 and output a signal representative of the intensity of IR energy 138. Although IR energy 138 may be emitted in several directions from portion 136, temperature sensor 132 may only detect the IR energy directly transmitted from portion 136.

In some examples, the emissivity of portion 136 of heat pipe 130 may differ from the emissivity of portion 134 of housing 122. This emissivity difference may arise from the materials used for heat pipe 130 and housing 122 being dissimilar. For example, housing 122 may be constructed of a titanium alloy and heat pipe 130 may be constructed of copper or a copper alloy. The material may be solid, hollow, or any other continuous material configuration. In other words, heat pipe 130 may be constructed of a material with higher thermal conductivity than the material used in housing 122. Therefore, a processor may calibrate temperature sensor 132 to account for differences in emissivity between heat pipe 130 and housing 122. Such calibration may be performed instead of, or in addition to, use of a mathematical function for deriving the heat of portion 134 from the heat sensed from portion 136.

Heat pipe 130 may be configured within housing 122 to physically contact portion 134 of housing 122. In one example, heat pipe 130 may be mounted directly to housing 122 via conductive adhesive, spot welding, or any other technique. In another example, heat pipe 130 may be mounted to hybrid board 124 or another location internal to housing 122. In this example, heat pipe 130 may be constructed such that a free end of heat pipe 130 is biased against portion 134 of housing 122 when housing 122 is hermetically sealed around the interior components of IMD 120. In other words, closing housing 122 may cause portion 134 to contact heat pipe 130 such that the structural stiffness of heat pipe 130 retains physical contact between heat pipe 130 and portion 134.

As shown in FIG. 5B, IMD 140 may include light pipe 152 instead of heat pipe 130 for transferring energy from a desired portion of IMD 140. IMD 40 may be substantially similar to IMD 120 of FIG. 5A. IMD 140 may include housing 142 that encloses hybrid board 144, electronics 146 and 148, and temperature sensor 150. Temperature sensor 150 may be mounted onto a surface of hybrid board 144. However, light pipe 152 may transfer IR energy 156 from portion 154 of housing 142 to temperature sensor 150.

Light pipe 152 may be disposed within housing 142 to transfer energy from 154 to temperature sensor 150. Light pipe 152 may or may not be thermally coupled to portion 154. However, in either case, heat conducted through materials of light pipe 152 may not be used to sense the temperature of portion 154. Instead, light pipe 152 may be a conduit for transferring IR energy 156 from portion 154 to temperature sensor 150. Light pipe 152 may include an optical fiber, a series of mirrors, or any other reflective conduit that transmits IR energy 156 emitted from portion 154. In other words, IR energy 156 may be transmitted within light pipe 156. Although light pipe 152 may be flexible, light pipe 152 may instead be a substantially rigid structure mounted to temperature sensor 150 and/or hybrid board 144. Light pipe 152 may be physically separated from portion 154, but an open end of light pipe 154 may be sufficiently proximal to portion 154 such that only IR energy 156 from the desired portion 154 enters light pipe 152. In other examples, light pipe 154 may physically contact portion 154.

In other examples, a single device may include multiple heat pipes and/or multiple light pipes. In this manner, temperatures from several different portions of the device may be sensed using any of the structures or techniques described herein.

Figure 6:
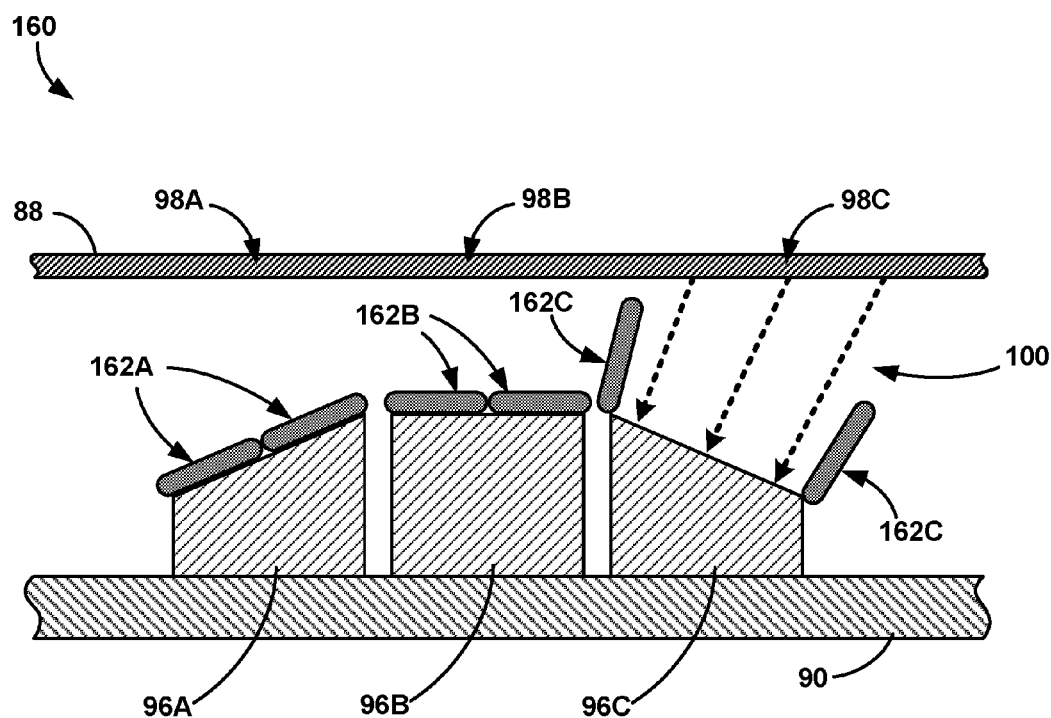
FIG. 6 is a conceptual diagram illustrating example temperature sensors and respective shutters for selectively sensing temperature from different portions of an IMD.

FIG. 6 is a conceptual cross-sectional diagram illustrating example temperature sensors 96 and respective shutters 162 for selectively sensing temperature from different portions of IMD 160. IMD 160 is an example of IMD 86 of FIG. 4B. IMD 160 may include three IR temperature sensors 96A, 96B, and 96C mounted to hybrid board 90. However, each of temperature sensors 96 may include a pair of shutters controlled by a processor to selectively allow IR energy to enter one or more of sensors 96.

Shutters 162A may cover an aperture of temperature sensor 96A, shutters 162B may cover an aperture of temperature sensor 96B, and shutters 162C may cover an aperture of temperature sensor 96C. Each of shutters 162 may block IR energy transfer and be coupled to a motor or actuator that opens and closes the respective shutter on demand. In other examples, one or more of shutters 162 may be electro-optical such that a control signal can be applied to cause a material of the shutter to toggle between a transparent state and an opaque state. A processor within IMD 60 may control the shutters to open when that temperature sensor is selected to sense the temperature of a respective portion of housing 88. For example, shutters 162A may open to receive IR energy from portion 98A, shutters 162B may open to receive IR energy from portion 98B, and shutters 162C may open to receive IR energy from portion 98C.

As shown in FIG. 6, shutters 162A and 162B are closed to prevent temperature sensors 96A and 96B, respectively, from sensing temperature of portions 98A and 98B. However, shutters 162C are open to allow IR energy 100 to enter the aperture of temperature sensor 96C. Temperature sensor 96C has thus been selected to sense the temperature of portion 98C. Not only may shutters 162C allow IR energy 100 from portion 98C to be detected by sensor 96C, shutters 162C may block IR energy from other locations to be detected by temperature sensor 96C. In other words, shutters 162C may reduce any infrared radiation emitted from non-target surfaces. Shutters 162C may thus be positioned to only accept IR energy from a desired surface of IMD 160.

Shutters 162 may, as shown in the example of FIG. 6, be rectangular in shape and operate in pairs. In some examples, each temperature sensor 96 may include a single shutter. In other examples, each temperature sensor 96 may include two or more shutters. For example, the shutters may be positioned circumferentially around a temperature sensor such that each shutter slides over another shutter to open or close the aperture of the temperature sensor. This type of circular shutter may be similar to a shutter for an aperture of a camera.

In some examples, each of temperature sensors 96 may be independent sensors. Alternatively, temperature sensors 96 may be coupled together and output a single signal to a processor. The output may thus be the result of IR energy received from each sensor. In this manner, shutters 162 may be selectively opened or closed such that the output signal is only representative of the desired portion 98A, 98B, and/or 98C. Although shutters 162 are described with respect to temperature sensors 96 within IMD 160, shutters may alternatively be used in other medical devices, such as charging device 22.

In other examples, one or more of shutters 162 may be constructed of a material that can be used to calibrate the output of one or more of temperature sensors 96. This material may be a "black body" that emits infrared radiation at a level independent of the temperature of the material. In other words, for at least the temperature ranges expected within IMD 160, the emissivity of the black body (e.g., shutters 162) may be approximately constant. The processor of IMD 160 may then calibrate the output of sensors 96 to the known temperature represented by the infrared radiation from shutters 162. IMD 160 may perform this calibration periodically, every time shutters 162 close, or on command from charging device 22 or another programming device. This calibration may also be performed during the manufacturing process for IMD 160.

Figure 7:
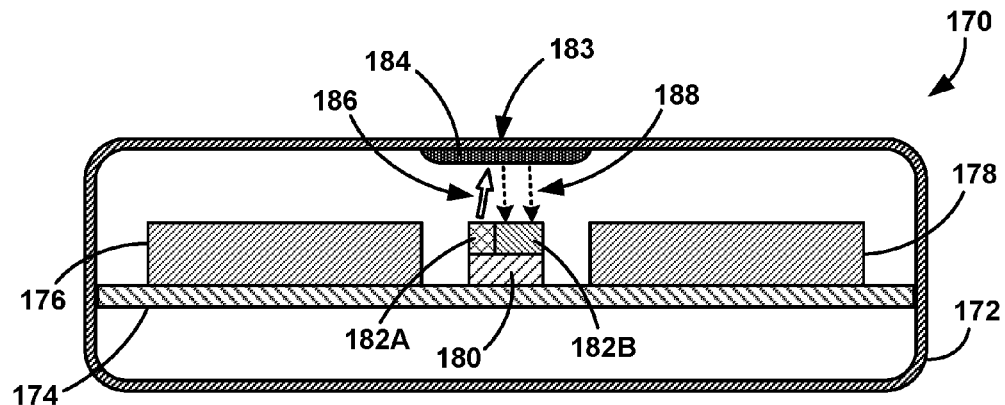
FIG. 7 is a conceptual diagram illustrating an example temperature sensor utilizing phosphor thermometry.

FIG. 7 is a conceptual cross-sectional diagram illustrating temperature sensor 180 utilizing phosphor thermometry. IMD 170 may be an example of IMD 14. As shown in FIG. 7, IMD 170 includes housing 172 that encloses hybrid board 174, electronics 176 and 178, and temperature sensor 180. Hybrid board 174 may be mounted or secured within housing 172. Electronics 176 and 178 may include various components such as a processor and memory. Although not shown in FIG. 7, a secondary coil and rechargeable power source may also be disposed within housing 172. Temperature sensor 180 may be mounted onto a surface of hybrid board 174.

Temperature sensor 180 may be a phosphor temperature sensor that is oriented in a specific manner to detect the temperature of portion 183 of housing 172 using luminescence detected from phosphor material 184. In other words, temperature sensor 180 may be a non-thermally coupled temperature sensor that utilizes phosphor thermometry. Temperature sensor 180 may include emitter 182A and detector 182B. Emitter 182 emits electromagnetic radiation 186 toward phosphor material 184 disposed on the desired surface or portion 183. Emitted electromagnetic radiation 186 then excites phosphor material 184 disposed on portion 183. A characteristic of this excitation may be used to determine temperature. In other words, the object from which temperature will be sensed (e.g., portion 183) may be coated with phosphor material 184 which is excited such that characteristic of the excitation may be used to determine the temperature.

Detector 182B of temperature sensor 180 may be configured to detect luminescence 188 from phosphor material 184. Based on the temperature of phosphor material 184, and the thermally coupled portion 183, the luminescence will have a phase shift with respect to the excitation signal (e.g., radiation 186), when the excitation signal is periodic. The phase shift may have a magnitude that is representative of the temperature. In some examples, the magnitude will decay faster for higher temperatures. Temperature sensor 180 detects this phase shift in the detected luminescence 188 of phosphor material 184 that occurs in response to the excitation from electromagnetic radiation 186. Temperature sensor 180 may then determine the temperature of portion 183 based on the detected phase shift. In other examples, temperature sensor 180 may output a signal representative of the detected phase shift, and a processor (e.g., processor 30 or 50) is configured to determine the temperature based on the signal output from sensor 180.

Phosphor material 184 may be selected based on the anticipated temperatures of housing 172 or the object to which phosphor material 184 will be disposed. In some examples, phosphor material 184 may be europium doped lanthanum oxysulphide ($La_2O_2S$:Eu) or europium doped gadolinium oxysulphide ($Gd_2O_2S:Eu$). In addition, the emitted electromagnetic radiation 186 may be selected for the anticipated temperatures to be sensed. In general, electromagnetic radiation 186 may have a wavelength between approximately 430 nanometers (nm) and 620 nm. In one example, the wavelength of electromagnetic radiation 186 may be approximately 514 nm. Generally, as the temperature increases, the phase shift may be decreased.

Figure 8:
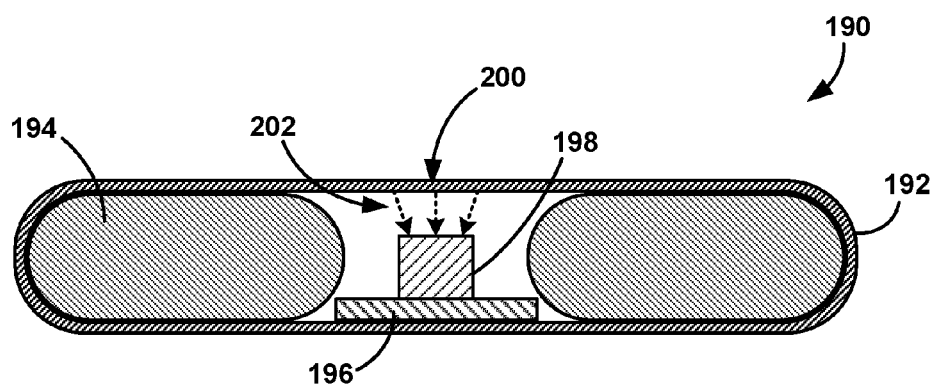
FIG. 8 is a conceptual diagram illustrating an example temperature sensor disposed within an external charging device.

FIG. 8 is a conceptual cross-sectional diagram illustrating temperature sensor 198 disposed within external charging device 22. Specifically, temperature sensor 198 may be disposed within charging head 190 of a charging device. Charging head 190 may be an example of charging head 26. However, in other examples, temperature sensor 198 may be disposed within another housing of charging device 22 or charging head 190 may be disposed within an external charging device.

As shown in FIG. 8, charging head 190 may include housing 192 that encloses hybrid board 196, temperature sensor 198, and primary coil 194. Primary coil 194 may be an example of primary coil 48 of FIG. 3. Temperature sensor 198 may be mounted onto a surface of hybrid board 196. Temperature sensor 198 may also be an IR temperature sensor oriented in a specific manner to detect infrared radiation emitted from a desired location of housing 192 (e.g., portion 200). Portion 200 may emit IR energy 202 that is detected by temperature sensor 198. Temperature sensor 198 may then output a signal that changes based on the changes to the IR energy 202 emitted from portion 200.

Although temperature sensor 198 is oriented to sense the temperature of portion 200 of housing 192, temperature sensor 198 may instead be oriented to sense the temperature of primary coil 194 or some other portion of the device. In any case, temperature sensor 198 may sense the temperature of charging head 190 during a charging session to identify the heat being applied adjacent to a patient's skin. In other examples, charging head 190 may include multiple temperature sensors, heat pipes, light pipes, or any other technique described herein (e.g., phosphor thermometry).

Figure 9:
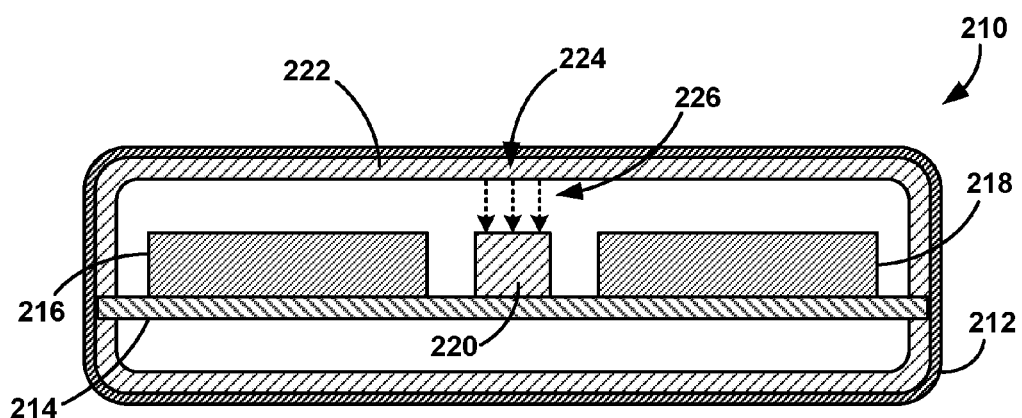
FIG. 9 is a conceptual diagram illustrating an example temperature sensor configured to detect the temperature of a phase change material disposed within an IMD.

FIG. 9 is a conceptual cross-sectional diagram illustrating example temperature sensor 220 configured to detect the temperature of phase change material 222 disposed within an IMD 210. IMD 210 may be similar to IMD 70 of FIG. 4A. However, IMD 210 may include phase change material 222 disposed within housing 212. As shown in FIG. 9, IMD 210 includes housing 212 that encloses hybrid board 214, electronics 216 and 218, and temperature sensor 220. Hybrid board 214 may be mounted or secured within housing 22. Electronics 216 and 218 may include various components such as a processor and memory. Although not shown in FIG. 9, a secondary coil and rechargeable power source may also be disposed within housing 212. Temperature sensor 220 may be mounted onto a surface of hybrid board 214.

Temperature sensor 220 may be an infrared temperature sensor oriented in a specific manner to detect infrared radiation emitted from a desired location of housing 212. Portion 224 may be an area of phase change material 222, adjacent to temperature sensor 220, from which the temperature is to be sensed. As described herein, portion 224 may emit IR energy 226 as a function of the temperature of portion 224. The temperature of phase change material 222 may by a function of the temperature of housing 212 when phase change material 222 is thermally coupled to housing 212. As IR energy 226 is emitted from portion 224, temperature sensor 220 may detect at least some of IR energy 226 and output a signal representative of the intensity of IR energy 226.

Phase change material 222 may be provided for several reasons. For example, phase change material 222 may absorb heat generated in IMD 210 during the charging session. Phase change material 222 may change between solid and liquid phases to absorb heat without increasing the temperature of IMD 210. In addition, phase change material 222 may disperse heat from various locations of IMD 210 to reduce temperature variations of housing 212. Therefore, the temperature sensed by temperature sensor 220 may be representative of a larger surface area of housing 212.

Furthermore, phase change material 222 may be selected such that the melting point of phase change material 222 is a temperature above which power levels for the charging session may be decreased. In other words, a processor may track changes in temperature to identify when phase change material 222 has fully changed phase and the temperature of IMD 210 may be approaching undesirable levels. The temperature curve may be monitored for inflection points that indicate energy is increasing temperature instead of changing phase of phase change material 222, for example. This temperature monitoring may eliminate the need for calibration of temperature sensor 220 and/or avoid inaccurate measurements in temperature.

When a charging session first begins, the temperature of IMD 210 and phase change material 222 may increase. When phase change material 222 begins to change phase, the sensed temperature from portion 224 may remain at a relatively constant temperature during the charging session substantially throughout the phase change. Once phase change material 222 has completely changed phase, the sensed temperature from portion 224 may again begin to rise. At this second inflection point in the sensed temperature, a processor may determine that the power level for charging may be decreased or even terminated to prevent additional increases in the temperature of housing 212. Since the sensed temperatures are dependent upon known properties of phase change material 222, the output from temperature sensor 220 may not need to be calibrated during use of IMD 210. Changes to the detection circuitry of temperature sensor 220 and/or electrical drift during measurement may not affect the temperature readings. Instead, the processor may merely monitor changes to the output signal from temperature sensor 220.

In another example, phase change material 222 may be used to calibrate temperature sensor 220 when IMD 210 is implanted within patient 12. Since the melting point or temperature at which phase change material 222 changes phase is known, the output from temperature sensor 220 may be calibrated based on when phase change material 222 changes phases. IMD 210 or charging device 22 may perform this calibration during each recharge session, after a predetermined number of recharging sessions, or according to a predetermined amount of time since the last calibration (e.g., a day, week, month, or year).

Phase change material 222 may be any compound or substance selected to change phases (e.g., change from a solid state to a liquid state) at a temperature within the operating temperatures of IMD 210 or the device within which phase change material 222 is used. Generally, the melting point of the phase change material may be lower than a temperature that would be uncomfortable to patient 12. For example, the phase change material may be selected to have a melting point between approximately 15 degrees Celsius and 50 degrees Celsius. More specifically, the phase change material may have a melting point between approximately 25 degrees Celsius and 45 degrees Celsius. In another example, the phase change material may have a melting point between approximately 35 degrees Celsius and 43 degrees Celsius.

Phase change material 222 may be selected from any variety of materials having properties sufficient to perform the functions described herein. For example, the phase change material may be a paraffin wax, a fatty acid, ester (carboxylic acid), inorganic materials such as salt hydrates or sodium hydrogen phosphate, or other compounds. The paraffin wax may be a saturated alkane having between 19 and 23 carbon atoms that have approximate melting points in a desired range. Example paraffin waxes may include nonadecane ($C_{19}H_{40}$; approximate melting point of 32.0 degrees Celsius), eicosane or N-eicosane ($C_{20}H_{42}$; approximate melting point of 36.4 degrees Celsius), heneicosane ($C_{21}H_{44}$; approximate melting point of 40.4 degrees Celsius), docosane ($C_{22}H_{46}$; approximate melting point of 44.4 degrees Celsius), or tricosane ($C_{23}H_{48}$; approximate melting point of 47.4 degrees Celsius). In one example, the phase change material selected for energy transfer device 26 may include eicosane. In some examples, the phase change material may include both eicosane and heneicosane The amount of phase change material included within energy transfer device 26 may be selected based on the power transferred by energy transfer device 26, the volume of IMD 210, the time needed for a charging session, and/or the desired temperature limit for IMD 210. The mass of phase change material 222 may also be based on the type of material selected. In some examples, IMD 210 may include between approximately 1.0 gram of phase change material and 100 grams of phase change material. However, more or less phase change material may be used in other examples.

As described herein, phase change material 222 and temperature sensor 220 may alternatively be disposed within charging head 26. When charging device 26 determines that phase change material 222 has exceeded a temperature threshold or the second inflection point in temperature has been identified, charging device 22 may terminate charging or instruct the user to terminate charging. In some examples, charging head 26 may be configured to be thermally coupled to phase change material cartridges that are replaceable by the user. Therefore, charging device 22 may present an instruction to the user to replace the heated cartridge with a new cartridge when the temperature exceeds a threshold or the temperature begins to rise again once the material has completely changed phase. This phase change material cartridge may allow the user to continue a charging session for longer durations.

Figure 10:
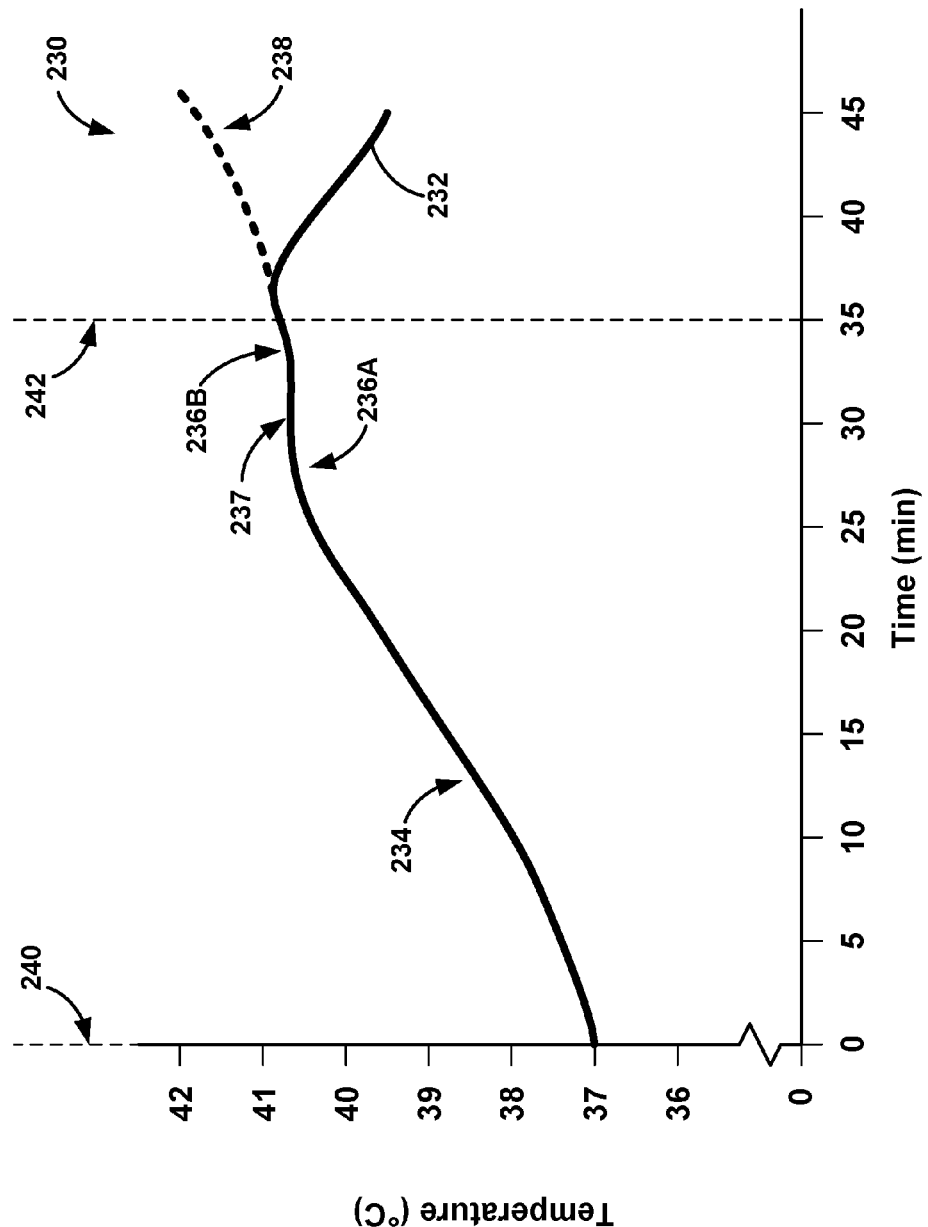
FIG. 10 is a graph of example temperatures generated in a patient during IMD recharging over a period of time using a phase change material cartridge exchange.

FIG. 10 is a graph 230 of example temperatures generated in a patient during IMD recharging over a period of time using a phase change material cartridge exchange. As shown in FIG. 10, graph 230 includes temperature 232 over time during recharging of rechargeable power source 18. This temperature may be sensed with a non-thermally coupled temperature sensor within charging head 26, for example. Therefore, temperature 232 may be representative of the temperature to which skin contacting charging head 26 may be subjected.

Graph 230 may indicate how temperature 232 changes when charging device 22 charges rechargeable power source 18 during a charging session. Once charging of rechargeable power source 18 begins at the zero minute mark (start period 240), temperature 232 begins to increase from approximately 37 degrees Celsius. Charging device 22 may transmit power to rechargeable power source 18 such that the temperature 232 rises at a temperature change rate 234. Once the phase change material of the cartridge begins to change phase (e.g., change from a solid to a liquid), the temperature change rate may decrease to temperature change rate 236B. The area of the curve between temperature change rates 235 and 237 may be identified as inflection point 236A.

Once the phase change material completely changes phases from the solid to the liquid phase, temperature 232 may again increase. Inflection point 236B identifies this increase to the temperature change rate. Once charging device 22 identified inflection point 236B, charging device 22 may present a notification to the user to replace the phase change material cartridge. After the user replaces the phase change material cartridge at cartridge change 242 (e.g., at approximately 35 minutes into the charging session), temperature 232 may begin to decrease as the new cartridge acts as a heat sink for the heat of charging head 26. Charging device 22 may detect subsequent increases to the temperature change rate and again present a notification to the user to change the phase change material cartridge.

If the user does not change the phase change material cartridge, temperature 232 may continue to increase along temperature curve 238. Charging device 22 may continue to monitor the sensed temperature and reduce the power level of charging or terminate charging if temperature 232 exceeds a temperature threshold. In this manner, charging device 22 may provide a safety override for charging if the user fails to change the phase change material cartridge.

Temperature 232 of graph 230 is only an example of tissue temperature changes due to charging rechargeable power source 18. In the example of FIG. 10, temperature 230 may increase to approximately 40.5 degrees Celsius prior to presenting the cartridge change notification to the user. In other examples, temperature 232 may change at faster or slower rates. In addition, temperature 232 may plateau at lower temperatures, plateau at higher temperatures, or not plateau at all during the recharge session. In some examples, temperature 232 may reach temperatures in excess of 42 degrees Celsius or even 43 degrees Celsius.

Temperature 232 of graph 230 may also apply to temperatures in other devices used to charge rechargeable power source 18. For example, IMD 210 may be subject to similar temperatures during charging. In addition, a processor may similarly identify inflection point 236B in IMD 210 to adjust the power level during charging or terminate charging as described with respect to FIG. 9. In other examples, example temperatures of graph 230 may also apply to devices without a phase change material.

Figure 11:
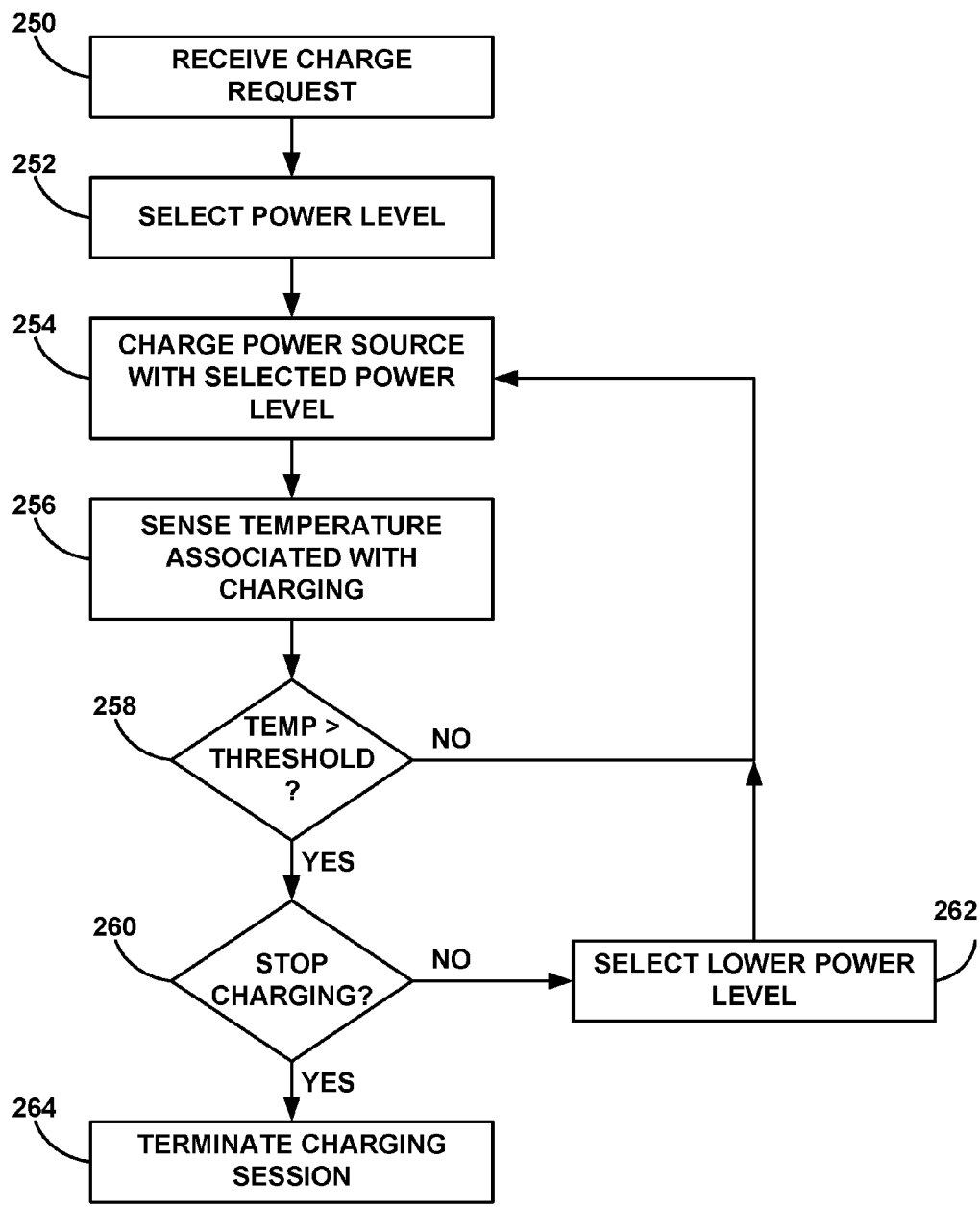
FIG. 11 is a flow diagram that illustrates an example technique for controlling the charging of an implantable rechargeable power source based on a sensed temperature.

FIG. 11 is a flow diagram that illustrates an example technique for controlling the charging of implantable rechargeable power source 18 based on a sensed temperature. Although processor 50 of charging device 22 will be described as generally performing the technique of FIG. 11, the technique of FIG. 11 may instead be performed by a combination of processors 30 and 50, in other examples. The technique of FIG. 11 may be applied to temperatures sensed by non-thermally coupled temperature sensors disposed within implantable device and/or external devices (e.g., external charging device 22 or charging head 26) associated with charging an implanted medical device.

A charging session for rechargeable power source 18 may begin when processor 50 receives a charge request via user interface 54 (250). Processor 50 may select the power level for charging (e.g., a high power level) (252). Processor 50 may then control charging device 22 to charge power source 18 with the selected power level (254). During charging, temperature sensor 39 may sense the temperature of a portion of IMD 14 using non-thermal coupling (e.g., non-contact) techniques described herein (256). Processor 30 may transmit the sensed temperatures to charging device 22 via telemetry modules 36 and 56. As long as the sensed temperature remains below or equal to the threshold ("NO" branch of block 258), processor 50 may continue to charge power source 18 with the high power level (254).

In response to the sensed temperature becoming greater than the threshold ("YES" branch of block 258), processor 50 may determine if charging is to stop (260). For example, processor 50 may have received a stop charging command from the user, power source 18 may be fully recharged, or the charging session may be stopped for any other reason. If processor 50 is not to stop charging ("NO" branch of block 260), processor 50 may select a lower power level (262) and continue to charge power source 18 (256). This lower level may be a trickle charge, a cycled (on/off) charge or other power level that does not increase the temperature of charging head 26 or IMD 14 above a desired temperature threshold. If processor 50 determines that the charging session is to be stopped ("YES" branch of block 260), processor 50 may terminate the charging session (264).

In this manner, processor 50 may control the charging of rechargeable power source 18 based on the sensed temperatures from one or more non-thermally coupled temperature sensor. In the case of multiple temperatures, processor 50 may control the charging based on the temperature sensor outputting the highest temperatures. In other examples, processor 50 may average or otherwise generate an overall temperature based on the multiple temperature measurements.

Figure 12:
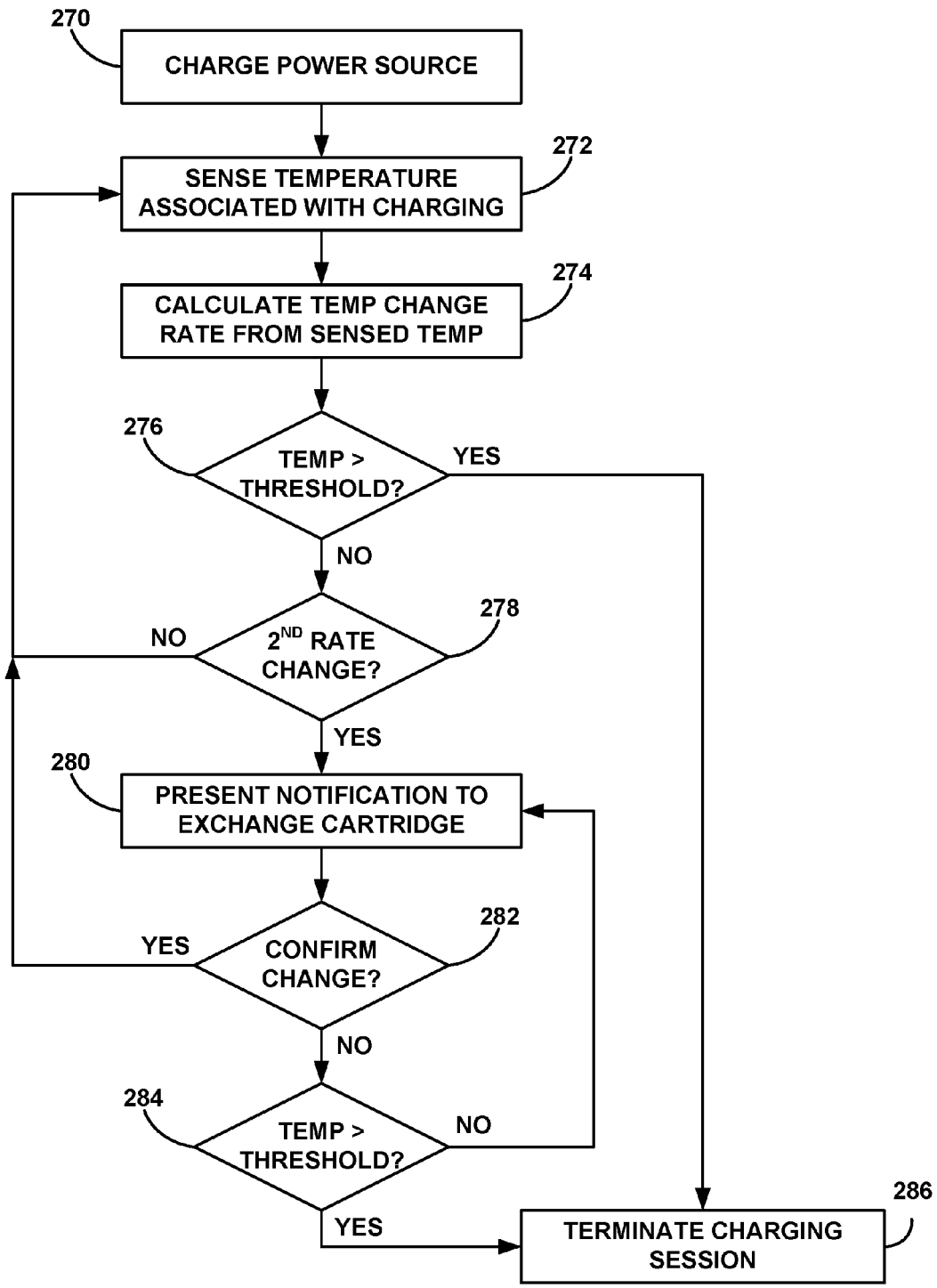
FIG. 12 is a flow diagram that illustrates an example technique for presenting a notification to a user for exchanging a phase change material cartridge.

FIG. 12 is a flow diagram that illustrates an example technique for presenting a notification to a user for exchanging a phase change material cartridge. Processor 50 of charging device 22 will be described as generally performing the technique of FIG. 12. However, other processors or devices may contribute to the technique of FIG. 12. The technique of FIG. 11 may be applied to temperatures sensed by non-thermally coupled temperature sensors disposed within charging device 22, charging head 26, or any other device that may include a replaceable heat sink.

Processor 50 may begin charging rechargeable power source 18 in response to receiving a command from a user or other received instructions (270). Using a non-thermally coupled temperature sensor within charging head 26 (e.g., temperature sensor 198 of IMD 190), processor 50 may sense the temperature of charging head 26 associated with the charging session (272). Processor 50 may then calculate a temperature change rate from the sensed temperatures (274). Processor 50 may also compare the sensed temperature to a threshold (276). If the sensed temperature exceeds a threshold ("YES" branch of block 276), processor 50 may terminate the charging session (286). The threshold may be used as a safety for when the user fails to replace the phase change material cartridge.

If the sensed temperature is less than or equal to the threshold ("NO" branch of block 276), processor 50 may determine if there has been a second temperature change rate change such as an inflection point in the sensed temperature (278). The first temperature change rate adjustment, or inflection point, may be due to the phase change material changing phase without increasing in temperature. The second temperature change rate change, or inflection point, may be due to the phase change material having fully changed from a solid phase to a liquid phase. If processor 50 does not detect the second rate change ("NO" branch of block 278), processor 50 may continue to sense the temperature of charging head 26 (272).

In response to detecting the second rate change ("YES" branch of block 278), processor may present a notification to the user to exchange or replace the phase change material cartridge (280). The notification may be a visual message, an audible alert, or even a tactile vibration. In response to receiving a confirmation input from a user that confirms the cartridge has been changed ("YES" branch of block 282), processor 50 may continue sensing the temperature (272). If processor 50 has not received a confirmation input ("NO" branch of block 282), processor 50 may compare the sensed temperature to a threshold such as the threshold in block 276 (284). If the sensed temperature is less than or equal to the threshold ("NO" branch of block 284), processor 50 may continue to present the notification (280) and wait for the confirmation input. In response to determining that the sensed temperature has exceeded the threshold ("YES" branch of block 284), processor 50 may terminate the charging session (286).

Figure 13:
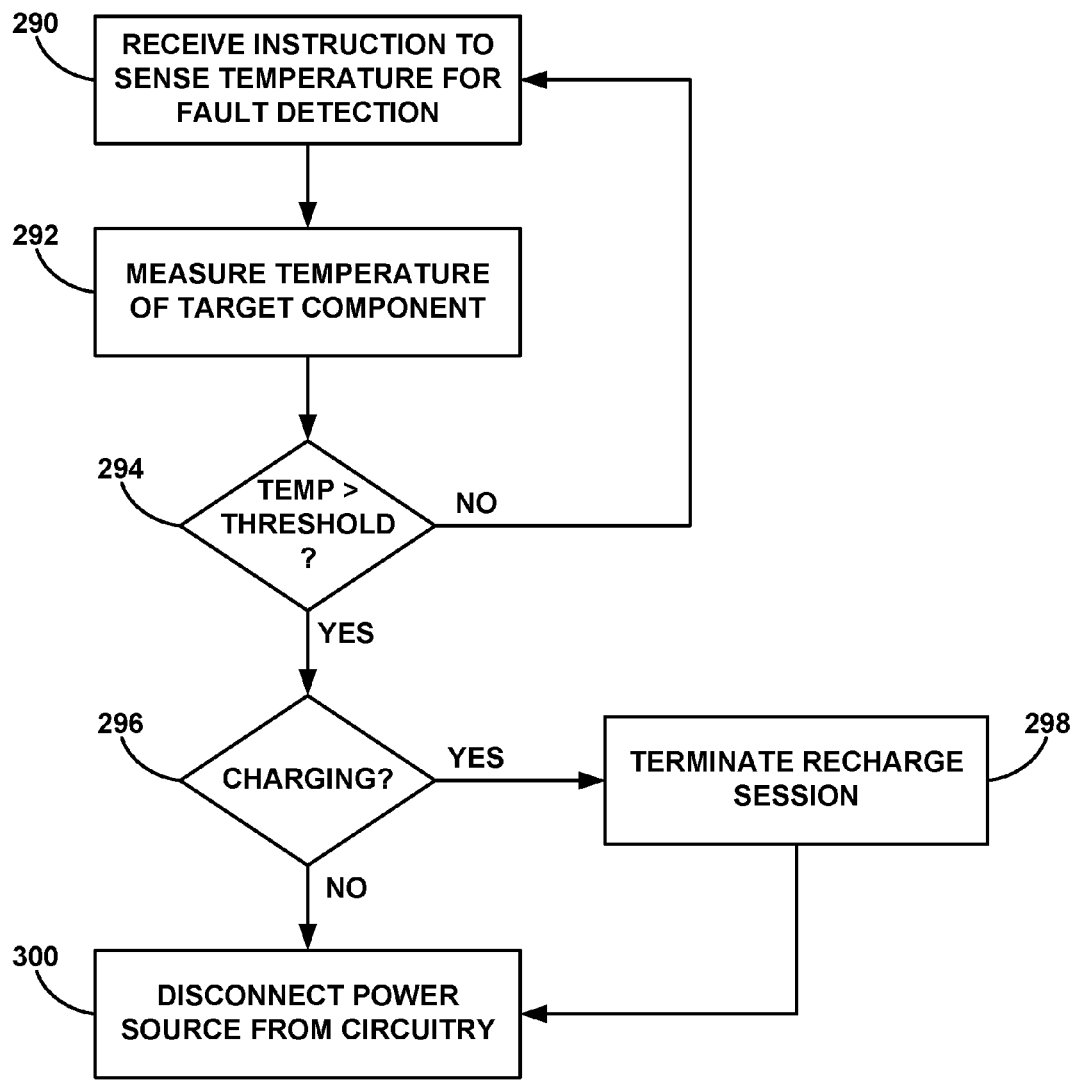
FIG. 13 is a flow diagram that illustrates an example technique for detecting a fault condition of a medical device component.

FIG. 13 is a flow diagram that illustrates an example technique for detecting a fault condition of a medical device component. Processor 30 of IMD 14 will be described as generally performing the technique of FIG. 13. However, other processors or devices (e.g., processor 50 of external charging device 22) may contribute to or separately perform the technique of FIG. 13.

Processor 30 may receive an instruction to sense temperature for fault condition detection of one or more circuits within IMD 14 (290). Processor 30 may then instruct temperature sensor 39 to measure the temperature of a target component (292). The target component may be a portion of an electrical circuit, a component coupled to a circuit (e.g., power source 18), or a surface of the housing that houses one or more electrical circuits that may be subject to a fault condition.

The fault condition may be indicative of excess current present within one or more electrical circuits of IMD 14. These electrical circuits may include processor 30, temperature sensor 39, and or other components that perform one or more functions for IMD 14. Excess current, e.g., a fault condition, may increase the temperature of one or more components within IMD 14 and potentially damage an electrical circuit or other electrical coupled component. Although the temperature may be sensed for the specific purpose of monitoring and detecting a possible fault condition, the temperature may instead be a sensed temperature measured for any general purpose.

Processor 30 may then compare the sensed temperature to a fault condition threshold (294). If the sensed temperature is less than the fault condition threshold ("NO" branch of block 294), processor 30 may wait until the next instruction to sense the temperature for fault condition detection (290). If the sensed temperature is greater than or equal to, or otherwise exceeds, the fault condition threshold ("YES" branch of block 294), processor 30 may determine if rechargeable power source 18 is being charged (296). The fault condition threshold may be a stored temperature (e.g., approximately 43 degrees Celsius) that may indicate a fault has occurred within an electrical circuit that is producing excess current and resulting in increased temperatures. In other examples, the fault condition threshold may be a representation of the temperature over time. For example, the fault condition threshold may be a rate of temperature change, a magnitude of temperature change over a predetermined period of time, or other equations representative of how the temperature has changed. Temperature change over time may be indicative of a fault condition instead of another condition during operation of IMD 14. For example, quickly rising temperatures may be more indicative of a fault condition than slower rising temperatures associated with recharging power source 18.

If a charging session is occurring to charge power source 18 ("YES" branch of block 296), processor 30 may terminate the recharge session (298). Processor 30 may terminate the recharge session by transmitting a termination request to external charging device 22. Alternatively, processor 30 may open a switch between coil 40 and power source 18 that prevents further charging of power source 18. Processor 30 may then disconnect power source 18 from at least one electrical circuit of IMD 14 (300). If no charging session is currently occurring ("NO" branch of block 296), processor may disconnect power source 18 from at least one electrical circuit of IMD 14 (300). Disconnection of power source 18 may immediately reduce temperatures of IMD 14 by reducing or terminating current flow within IMD 14. Processor 30 may disconnect power source 18 from the at last one electrical circuit by opening a switch between power source 18 and the at least one electrical circuit. In some examples, processor 30 may or may not be included in an electrical circuit disconnected from power source 18.

Processor 30 may periodically check for a fault condition using the sensed temperature from temperature sensor 39. In some examples, processor 30 may perform the fault detection process prior to starting a recharge session. If the sensed temperature is greater than the fault condition threshold, processor 30 may instruct charging device 22 to withhold any power transmission for recharging power source 18. In other examples, processor may detect a severity of the fault condition (e.g., the magnitude of the excess current within IMD 14). If the fault condition is minimal, processor 30 may limit certain functions to prevent the fault condition from raising temperatures or damaging any circuits. A minimal fault condition may also trigger processor 30 to limit the current used to charge power source 18 and/or command charging device 22 to limit the power level used to charge power source 18. In addition to sensing temperature to detect a fault condition, processor 30 may monitor current values within one or more electrical circuits that may indicate a fault condition. In this manner, processor 30 may have redundant or backup sensing methods to ensure detection of a fault condition or confirm that a fault condition has occurred.

In other examples, processor 30 may utilize two or more temperature sensors to sense the temperature of different surfaces within IMD 14. For example, processor 30 may measure the temperature at multiple portions of the housing. Processor 30 may compare one or more of the measured temperatures to respective fault condition thresholds (or a single threshold) and determine which of the temperatures exceed the respective threshold. Based on which temperature(s) exceeds the threshold, processor 30 may identify or estimate which component within IMD 14 is responsible for creating the fault condition. Processor 30 may reduce the functionality of this component, reduce the current to this component, shut down the component, or otherwise selectively alter electrical currents within the electrical circuitry to remedy the fault condition of the identified component.

Figure 14:
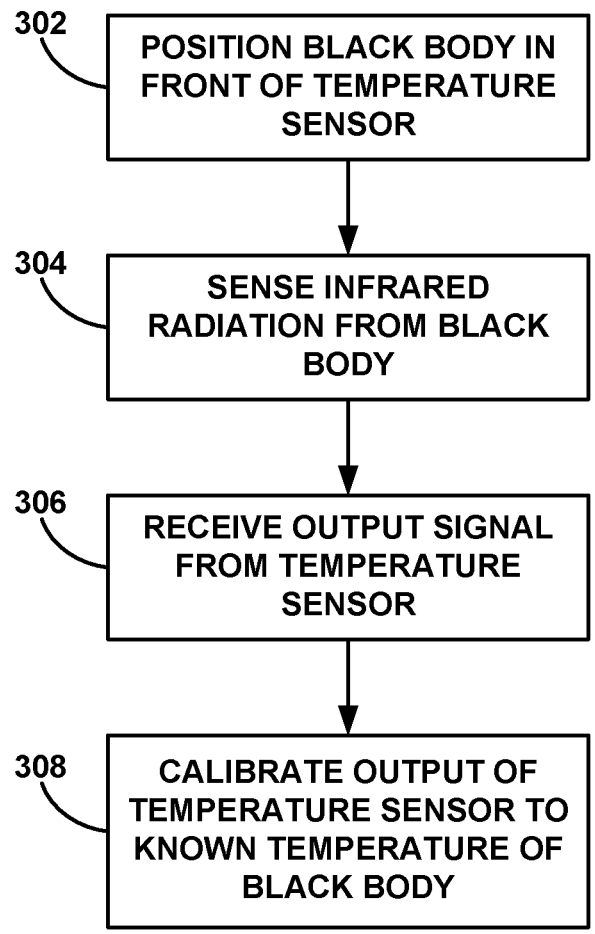
FIG. 14 is a flow diagram that illustrates an example technique for calibrating a non-thermally coupled temperature sensor.

FIG. 14 is a flow diagram that illustrates an example technique for calibrating a non-thermally coupled temperature sensor. The process of FIG. 14 will be described with respect to manufacturing IMD 14 within non-thermally coupled temperature sensor 39. However, this calibration process may additionally or alternatively be performed by processor 30 of IMD 14 or processor 50 of external charging device 22 during operation of the device using a non-thermally coupled temperature sensor (e.g., temperature sensors 39 and/or 59) described herein. For example, a shutter may be a black body that moves over the temperature sensor within the device.

When manufacturing IMD 14, temperature sensor 39 may be calibrated such that the output signal from temperature sensor 39 is mapped to the temperature sensed by temperature sensor 39 when the output signal was produced. A calibration machine or a user may position a "black body" in front of the temperature sensor 39 to be calibrated (302). The black body may be a material that emits infrared radiation at a rate and magnitude independent of the temperature of the material. In other words, the emissivity of the black body may be relatively constant independent of ambient temperature. Although the emissivity may change due to large variations in temperature, the emissivity may remain relatively constant over the temperature ranges to which IMD 14 is normally subjected (e.g., 20 degrees Celsius to 43 degrees Celsius). In this manner, temperature sensor 39 may be calibrated without maintaining a specific ambient temperature within which temperature sensor 39 and the black body must be calibrated.

Once the black body is placed within sensing range of temperature sensor 39, temperature sensor 39 may be controlled to sense the infrared radiation from the black body (304). A processor (e.g., processor 30 or a processor of an external device) may receive the output signal from temperature sensor 39 (306). The processor may then calibrate the output of temperature sensor 39 to the known temperature of the emissivity of the black body (308). For example, if the infrared emissivity of the black body represents a temperature of 37 degrees Celsius of the surface from which temperature sensor 39 will be sensing within IMD 14, the output of temperature sensor 39 may be calibrated to represent 37 degrees Celsius. This calibration process may be repeated with one or more black bodies of with different emissivities to create a calibration curve for temperature sensor 39 in some examples.

In some examples, the calibration of temperature sensor 39 may, but need not, be performed for each sensor being manufactured or for each medical device being manufactured. Since infrared temperature sensors may have minimal part-to-part variation, the output from one temperature sensor to another temperature sensor may be relatively equal. Therefore, the calibration process may only need to be performed for a batch of temperature sensors or even once during design of the temperature sensor. In this case, a universal calibration may be performed using one temperature sensor, and the universal calibration may be applied to all of the temperature sensors manufactured equivalently.

In other examples, a temperature sensor within the IMD (e.g., temperature sensor 39 in IMD 14) may be calibrated using a calibrated temperature sensor within an external device. For example, external charging device 22 may include a temperature sensor that is calibrated. When external charging device 22 is placed in contact with patient 12 and proximate to IMD 14, IMD 14 may utilize the sensed temperature from the calibrated temperature sensor to calibrate temperature sensor 39. Alternatively, charging device 22 may calibrate the output of temperature sensor 39 received from IMD 14.

In still another example, one or more temperature sensors may be calibrated during a first recharge session by monitoring a deflection point in the temperature curve associated with temperature of a phase change material as discussed above. This deflection point (e.g., point at which temperature plateau ceases and temperature rises following completion of phase change) may be associated with a known absolute temperature that may be used to calibrate one or more temperature sensors. Once this calibration is performed, charging device 22 may then begin the charging session.

Alternatively, non-thermally coupled temperature sensors may not need to be calibrated. Instead, a pair of temperature sensors may be utilized and common mode rejection used to determine a temperature difference instead of an absolute temperature value. In another example, a temperature difference from one sensor may be used instead of a calibrated absolute temperature. Since the temperature before a charging session may be approximately equal to normal body temperature, the system may use the relative change in temperature to determine how to control charging of IMD 14.

According to the techniques and devices described herein, an IMD or external charging device may include one or more temperature sensors (e.g., an IR sensor, phosphor temperature sensor, or any other sensor not requiring thermal coupling to determine temperature) configured to sense the temperature of a portion of the device not thermally coupled to the temperature sensor. These non-thermally coupled sensors may be mounted on a PCB or hybrid board and directed toward a specific surface to be sensed. In this manner, non-thermally coupled sensors may obtain temperature information about one or more portions of the device without being physically coupled to the portion of interest. The IMD and/or external charging device may then control charging of an implantable rechargeable power source using the sensed temperatures.

This disclosure is primarily directed to wireless transfer of energy between two coils (e.g., inductive coupling). However, one or more aspects of this disclosure may also be applicable to energy transfer involving a physical connection between a charging device and a rechargeable power supply. For example, aspects of this disclosure may be applicable to charging the power supply of an IMD by inserting a needle coupled to an external charging device through the skin and into a port of the IMD. Although physical connections for energy transfer may not introduce heat losses due to energy transfer between wireless coils, heat may still be generated and lost to the patient from components within the IMD (e.g., the battery being charged and circuits involved in the recharging of the power supply).

The disclosure also contemplates computer-readable storage media comprising instructions to cause a processor to perform any of the functions and techniques described herein. The computer-readable storage media may take the form of any volatile, non-volatile, magnetic, optical, or electrical media, such as a RAM, ROM, NVRAM, EEPROM, flash memory, or any other digital media. The computer-readable storage media may be non-transitory in that the storage media is not an electromagnetic carrier wave. However, this does not mean that the storage media is not transportable or that it non-volatile. A programmer, such as patient programmer or clinician programmer, may also contain a more portable removable memory type to enable easy data transfer or offline data analysis.

The techniques described in this disclosure, including those attributed to IMD 14, charging device 22, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated, discrete, or analog logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 30 of IMD 14, processor 50 of charging device 22, or any one or more parts of the techniques described herein may be implemented by a processor of one of IMD 14, charging device 22, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

Various examples have been described. These and other examples are within the scope of the following claims.

What is claimed is:

1. A method comprising:
    sensing a temperature of a portion of a housing of a medical device by a temperature sensor disposed within the housing of the medical device, wherein the temperature sensor is configured to sense the temperature of the portion of the housing without being thermally coupled to the portion of the housing;
    determining, based on the sensed temperature, that a fault occurred with a component of the medical device; and
    responsive to determining that the fault occurred, controlling an operation associated with the medical device.

2. The method of claim 1, wherein controlling the operation associated with the medical device comprises controlling an external charging device to limit a power level of current generated by the external charging device that charges a rechargeable power source of the medical device.

3. The method of claim 2, wherein controlling the external charging device to limit the power level comprises controlling the external charging device to withhold power transmission to the rechargeable power source.

4. The method of claim 1, wherein controlling the operation associated with the medical device comprises limiting a functionality of one or more components of the medical device to prevent the temperature of the medical device from further rising due to the fault condition.

5. The method of claim 1, wherein controlling the operation associated with the medical device comprises reducing an electrical current delivered to a component identified as causing the fault.

6. The method of claim 1, wherein determining that the fault occurred comprises determining that the sensed temperature exceeds a fault condition threshold.

7. The method of claim 1, wherein determining that the fault occurred comprises determining that a rate of change of the sensed temperature exceeds a fault condition threshold rate of temperature change.

8. The method of claim 1, wherein determining that the fault occurred comprises determining that a magnitude of change of the sensed temperature over a predetermined period of time exceeds a fault condition threshold magnitude of temperature change over the predetermined period of time.

9. The method of claim 1, wherein sensing the temperature of the portion of the housing comprises sensing a first temperature of a first portion of the housing with a first temperature sensor, and wherein the method further comprises:
sensing a second temperature of a second portion of the housing with a second temperature sensor;
determining that at least one of the sensed first temperature or the sensed second temperature exceeds a fault threshold;
identifying, based on the at least one of the sensed first temperature or the sensed second temperature exceeds the fault threshold, a component of the medical device responsible for creating the fault, wherein controlling the operation associated with the medical device comprises controlling operation of the component to address the fault.

10. The method of claim 1, wherein sensing the temperature comprises sensing the temperature with the temperature sensor being mounted to a printed circuit board within the housing of the medical device.

11. A system comprising:
a medical device comprising a housing;
a temperature sensor disposed within the housing of the medical device and configured to sense a temperature of a portion of the housing of the medical device, wherein the temperature sensor is configured to sense the temperature without being thermally coupled to the portion of the housing; and
processing circuitry configured to:
determine, based on the sensed temperature, that a fault occurred with a component of the medical device; and
responsive to the determination that the fault occurred, control an operation associated with the medical device.

12. The system of claim 11, wherein the processing circuitry is configured to control the operation associated with the medical device by controlling an external charging device to limit a power level of current generated by the external charging device that charges a rechargeable power source of the medical device.

13. The system of claim 12, wherein the processing circuitry is configured to control the operation associated with the medical device by controlling the external charging device to withhold power transmission to the rechargeable power source.

14. The system of claim 11, wherein the processing circuitry is configured to control the operation associated with the medical device by limiting a functionality of one or more components of the medical device to prevent the temperature of the medical device from rising due to the fault condition.

15. The system of claim 11, wherein the processing circuitry is configured to control the operation associated with the medical device by reducing an electrical current delivered to a component identified as causing the fault.

16. The system of claim 11, wherein the processing circuitry is configured to determine that the fault occurred by determining that the sensed temperature exceeds a fault condition threshold.

17. The system of claim 16, wherein the processing circuitry is configured to determine that the fault occurred by determining that a rate of change of the sensed temperature exceeds a fault condition threshold rate of temperature change.

18. The system of claim 16, wherein the processing circuitry is configured to determine that the fault occurred by determining that a magnitude of change of the sensed temperature over a predetermined period of time exceeds a fault condition threshold magnitude of temperature change over the predetermined period of time.

19. The system of claim 11, wherein:
the temperature is a first temperature, the portion of the housing is a first portion of the housing, and the temperature sensor is a first temperature sensor,
the system further comprises a second temperature sensor configured to sense second temperature of a second portion of the housing, and
the processing circuitry is configured to:
determine that at least one of the sensed first temperature or the sensed second temperature exceeds a fault threshold;
identify, based on the at least one of the sensed first temperature or the sensed second temperature exceeds the fault threshold, a component of the medical device responsible for creating the fault; and
control the operation associated with the medical device by controlling operation of the component to address the fault.

20. The system of claim 11, further comprising a printed circuit board within the housing of the device, wherein the temperature sensor is mounted to the printed circuit board.

21. The system of claim 11, wherein the medical device comprises an implantable medical device that houses a stimulation generator and a rechargeable power source.

22. A system comprising:
means for sensing a temperature of a portion of a housing of a medical device without being thermally coupled to the portion of the housing, the means for sensing the temperature being disposed within the housing of the medical device;
means for determining, based on the sensed temperature, that a fault occurred with a component of the medical device; and
means for, responsive to determining that the fault occurred, controlling an operation associated with the medical device.

* * * * *